US012721502B2

(12) United States Patent
Hernandez et al.

(10) Patent No.: US 12,721,502 B2
(45) Date of Patent: Sep. 1, 2026

(54) CLEANING ADAPTER WITH AND WITHOUT SAFETY TAG

(71) Applicant: Medivators Inc., Minneapolis, MN (US)

(72) Inventors: Cesar E. Hernandez, Conroe, TX (US); John Wayne Miller, Magnolia, TX (US); Travis Bendele, Montgomery, TX (US); Joshua Lee Ronan, Willis, TX (US); Heba Hijazi, Pasadena, TX (US); Roger Garrett, Houston, TX (US); Robert Lagow, Shepard, TX (US)

(73) Assignee: Medivators Inc., Minneapolis, MN (US)

( * ) Notice: Subject to any disclaimer, the term of this patent is extended or adjusted under 35 U.S.C. 154(b) by 125 days.

(21) Appl. No.: 18/741,876

(22) Filed: Jun. 13, 2024

(65) Prior Publication Data

US 2024/0324855 A1 Oct. 3, 2024

Related U.S. Application Data

(63) Continuation of application No. 17/056,507, filed as application No. PCT/US2019/030888 on May 6, 2019, now Pat. No. 12,016,528.

(Continued)

(51) Int. Cl.
*A61B 1/00* (2006.01)
*A61B 1/12* (2006.01)

(Continued)

(52) U.S. Cl.
CPC ...... *A61B 1/00128* (2013.01); *A61B 1/00055* (2013.01); *A61B 1/00068* (2013.01);

(Continued)

(58) Field of Classification Search
CPC ............... G09F 3/02; G09F 2003/0222; G09F 2003/0269; G09F 2003/0276; G09F 3/04
See application file for complete search history.

(56) References Cited

U.S. PATENT DOCUMENTS 3,958,566 A 5/1976 Furihata
4,197,984 A * 4/1980 Hartman ................ B65D 75/54 40/310

(Continued)

FOREIGN PATENT DOCUMENTS

EP 0055394 3/1985
EP 1099393 5/2001

(Continued)

OTHER PUBLICATIONS

JP3828433B2—Oct. 4, 2022—Yasuta Ishibiki—Google Patents English Translation.

(Continued)

*Primary Examiner* — Gary C Hoge
(74) *Attorney, Agent, or Firm* — Sorell, Lenna & Schmidt, LLP

(57) ABSTRACT

A cleaning adapter for an endoscope is provided. The cleaning adapter comprises a main stem comprising a first through hole extending transversely through the main stem, a second through hole extending transversely through the main stem, and a channel within the main stem fluidly coupling the first through hole to the second through hole. In some embodiments, a tag for an endoscope valve is provided. Methods and kits are also provided.

9 Claims, 29 Drawing Sheets

Related U.S. Application Data

(60) Provisional application No. 62/674,336, filed on May 21, 2018.

(51) Int. Cl.
*G02B 23/24* (2006.01)
*G02B 27/00* (2006.01)
*A61B 90/70* (2016.01)

(52) U.S. Cl.
CPC ...... *A61B 1/00137* (2013.01); *A61B 1/00144* (2013.01); *A61B 1/122* (2013.01); *A61B 1/123* (2013.01); *A61B 1/125* (2013.01); *G02B 23/2476* (2013.01); *G02B 27/0006* (2013.01); *A61B 2090/701* (2016.02)

(56) References Cited

U.S. PATENT DOCUMENTS 4,261,343 A 4/1981 Ouchi et al.
4,325,362 A 4/1982 Ouchi et al.
4,361,138 A 11/1982 Kinoshita
4,402,310 A 9/1983 Kimura
4,412,531 A 11/1983 Chikashige
4,561,426 A 12/1985 Stewart
4,561,428 A 12/1985 Konomura
4,800,869 A 1/1989 Nakajima
D300,361 S 3/1989 Tokarz
4,844,052 A 7/1989 Iwakoshi et al.
4,852,551 A 8/1989 Opie et al.
4,900,305 A 2/1990 Smith
4,982,726 A 1/1991 Taira
5,127,909 A 7/1992 Shichman
5,133,336 A 7/1992 Savitt et al.
5,386,817 A 2/1995 Jones
5,390,435 A * 2/1995 Grody ..................... G09F 23/06 40/658
5,391,145 A 2/1995 Dorsey, III
5,522,796 A 6/1996 Dorsey, III
5,840,016 A 11/1998 Kitanao et al.
5,871,441 A 2/1999 Ishiguro et al.
5,876,326 A 3/1999 Takamura et al.
5,943,804 A * 8/1999 Linquist .................... G09F 3/04 40/637
6,095,971 A 8/2000 Takahashi
D432,230 S 10/2000 Utas
6,132,369 A 10/2000 Takahashi
6,145,233 A * 11/2000 Hickmott ................ G09F 3/206 40/645
6,286,179 B1 9/2001 Byrne
6,321,473 B1 * 11/2001 Klabunde ................. G09F 3/04 40/310
6,334,844 B1 1/2002 Akiba
6,346,075 B1 2/2002 Arai et al.
6,358,224 B1 3/2002 Tims et al.
6,383,132 B1 5/2002 Wimmer
D473,646 S 4/2003 Baillargeon
D473,941 S 4/2003 Cise et al.
6,786,865 B2 9/2004 Dhindsa
6,849,043 B2 2/2005 Kondo
6,874,517 B2 4/2005 Halstead et al.
6,908,429 B2 6/2005 Heimberger
6,984,204 B2 1/2006 Akiba
7,137,981 B2 11/2006 Long
7,220,226 B2 5/2007 Rovegno
D546,946 S 7/2007 Blake et al.
D565,731 S 4/2008 Eisenkolb et al.
7,406,791 B2 * 8/2008 Lienau ...................... G09F 7/00 116/200
7,481,764 B2 1/2009 Soutorine et al.
7,597,662 B2 10/2009 Litscher et al.
D624,646 S 9/2010 Peschke et al.
7,901,350 B2 3/2011 Yamazaki
D644,731 S 9/2011 Fangrow, Jr.
8,241,208 B2 8/2012 Jiang et al.
8,267,102 B2 9/2012 Onishi et al.
8,568,303 B2 10/2013 Yamane
8,821,389 B2 9/2014 Yamane
8,920,311 B2 12/2014 Labombard
9,125,550 B2 9/2015 Shener-Irmakoglu et al.
9,144,373 B2 9/2015 Kaye et al.
9,144,374 B2 9/2015 Maurice, Jr.
9,161,680 B2 10/2015 Bellofatto et al.
D750,235 S 2/2016 Maurice
9,247,862 B2 2/2016 Shen et al.
9,307,890 B2 4/2016 Ouchi
D757,259 S 5/2016 Duck et al.
D761,420 S 7/2016 Hayamizu
9,398,842 B2 7/2016 Furuta
9,408,523 B2 8/2016 Grudo et al.
9,414,742 B2 8/2016 Sato
D771,806 S 11/2016 Steele
9,492,066 B2 11/2016 Iwasaki
9,565,995 B2 2/2017 Nguyen et al.
9,585,545 B2 3/2017 Anderson et al.
9,636,002 B2 5/2017 Hatano
10,092,670 B2 10/2018 Mason
10,238,273 B2 3/2019 Xu et al.
10,448,814 B2 10/2019 Rebholz et al.
10,874,291 B2 12/2020 Viebach et al.
11,589,738 B2 2/2023 Anderson et al.
2003/0181905 A1 9/2003 Long
2004/0238014 A1 12/2004 Halstead et al.
2006/0041190 A1 2/2006 Sato
2006/0100485 A1 5/2006 Arai et al.
2006/0116552 A1 6/2006 Noguchi et al.
2006/0135851 A1 6/2006 Yamazaki .......... A61B 1/00137 600/156
2006/0276689 A1 12/2006 Litscher et al.
2007/0179432 A1 8/2007 Bar Or et al.
2008/0098637 A1 * 5/2008 Pratt ......................... G09F 3/04 40/673
2010/0187256 A1 * 7/2010 Draisma .............. B65D 23/065 40/310
2010/0240956 A1 9/2010 Secrest et al.
2011/0298169 A1 12/2011 Nguyen et al.
2012/0088975 A1 4/2012 Morimoto
2012/0091092 A1 4/2012 Adams et al.
2013/0138061 A1 5/2013 Yamane
2013/0303844 A1 11/2013 Grudo et al.
2013/0338442 A1 12/2013 Anderson et al.
2015/0196141 A1 * 7/2015 Rohrig ...................... A47F 7/28 248/318
2016/0058518 A1 3/2016 Mason
2016/0120395 A1 5/2016 Qi
2016/0143516 A1 5/2016 Xu et al.
2016/0227984 A1 8/2016 Hatano
2016/0309987 A1 10/2016 Grudo et al.
2016/0331214 A1 11/2016 Fujitani et al.
2016/0338577 A1 11/2016 Viebach et al.
2017/0347860 A1 12/2017 Still et al.
2019/0287429 A1 * 9/2019 Dawson .................. G09F 1/065
2022/0238044 A1 * 7/2022 Petryczka ............ G09F 3/0329

FOREIGN PATENT DOCUMENTS

EP 1099393 A1 5/2001
EP 000279039-0004 3/2005
ES 2237050 7/2005
GB 0715224 9/2007
JP S56143132 4/1980
JP 58-010031 A 1/1983
JP S5810031 1/1983
JP S5818884 4/1983
JP 60142835 A 7/1985
JP S61-124602 A 8/1986
JP S62-133929 A 6/1987
JP 62-189041 A 8/1987
JP S62189041 8/1987
JP H8-215137 A 2/1995
JP H0739512 2/1995
JP 07265260 A 10/1995
JP H08215137 8/1996

(56) References Cited

FOREIGN PATENT DOCUMENTS

| | | |
|---|---|---|
| JP | 08238211 A | 9/1996 |
| JP | 08-266461 A | 10/1996 |
| JP | H08266461 | 10/1996 |
| JP | 09-122069 A | 5/1997 |
| JP | H09122069 | 5/1997 |
| JP | 1998-248791 A | 9/1998 |
| JP | H10-24879 A | 9/1998 |
| JP | H10248791 | 9/1998 |
| JP | 2000217777 | 8/2000 |
| JP | 2000217777 A | 8/2000 |
| JP | 2001346761 A | 12/2001 |
| JP | 3828433 B2 | 10/2002 |
| JP | 2002306405 A | 10/2002 |
| JP | 2003-310542 A | 5/2003 |
| JP | 2003310542 | 11/2003 |
| JP | 2004-169805 A | 6/2004 |
| JP | 2002306405 | 6/2004 |
| JP | 2004223121 | 8/2004 |
| JP | 3599093 | 12/2004 |
| JP | S3651982 | 5/2005 |
| JP | 2005261512 A | 9/2005 |
| JP | 2006-55447 A | 2/2006 |
| JP | 2006-175175 A | 7/2006 |
| JP | 2006175175 | 7/2006 |
| JP | 3828433 | 10/2006 |
| JP | 2007-185276 A | 7/2007 |
| JP | 2007185276 | 7/2007 |
| JP | 2004223121 A | 8/2007 |
| JP | 4242142 | 3/2009 |
| JP | 4242142 B | 3/2009 |
| JP | 4583915 | 11/2010 |
| JP | 4583915 B2 | 11/2010 |
| JP | 4589315 B | 11/2010 |
| JP | 2011160825 A | 8/2011 |
| JP | 2013545555 A | 12/2013 |
| JP | 2014133011 A | 7/2014 |
| WO | 2009-016352 | 2/2009 |
| WO | 2009-016352 A2 | 2/2009 |

OTHER PUBLICATIONS

JP08238211A—Sep. 17, 1996—Asahi Optical Co Ltd.—English Abstract Only.

JP08238211A—Sep. 17, 1996—Asahi Optical Co Ltd.—Google Patents English Translation.

JP2014133011A—Jul. 24, 2014—Hoya Corp—English Abstract Only.

JP2014133011A—Jul. 24, 2014—Hoya Corp—Google Patents English Translation.

JP2001346761A—Dec. 18, 2001—Asahi Optical Co Ltd.—English Abstract Only.

JP2001346761A—Dec. 18, 2001—Asahi Optical Co Ltd.—Google Patents English Translation.

Reprocessing Summary and Guide for Fujinon/Fujifilm Flexible GI Endoscopes. Fujifilm Medical Systems USA Inc. Endoscopy Division. Wayne, NJ. Feb. 2018.

Olympus Reprocessing Manual / Instructions. 2009 Olympus Medical Systems Corp.

Fujifilm Endoscopes EG-L590ZW, EC-L590ZW/L Operation Manual (Cleaning, Disinfection and Storage). 2013 Fujifilm Corp.

Fujifilm Endoscope EC-600WL Operation Manual (Preparation and Operation). Fujifilm Corp. Jan. 2018.

Fujinon Electronic Video Endoscopes EVE 530/590 Series Operation Manual (Cleaning, Disinfection and Storage). Fujinon Corporation. Jan. 2015.

Pentax Owner's Manual Video GI Scopes EG-290Kp, EC-380MKp, EC-380MK2p, EC-380FKp, EC-380FK2p, EC-380LKp. Pentax Corporation. Nov. 2009.

Pentax Instructions for Use. Pentax Video GI Scopes 90i Series. Pentax Corp. Mar. 2014.

5.1 Preparing the equipment for reprocessing. Chapter 5: Reprocessing the Endoscope (and related reprocessing accessories). Olympus Evis Exera II TJF Type Q180V Reprocessing Manual. 2009.

Photo of Fuji and Olympus endoscope valves. Feb. 2016.

Pentax Owner's Manual Pentax Video GI Scopes EG-290Kp, EC-380LKp, Nov. 2009.

Photos of Pentax OF-B120 Suction Control Valve, Pentax OF-B188 Air/Water Feeding Valve and Pentax OF-B121 Air/Water Valve, 2009.

Photos of Olympus Suction Valve MH-443 with parts separated, 2003.

Photos of Olympus Air/Water Valve MH-438 with parts separated, 2003.

Photo of Olympus suction valve MH-443 from internet website www.partsfinder.com, website visited Jan. 8, 2019 at https://www.partsfinder.com/parts/olympus-america-inc/MH443.

Photo of Olympus air/water valve MH-438 from internet website www.dotmed.com, website visited Jan. 8, 2019 at https://www.dotmed.com/listing/endoscope/olympus/mh-438/2101261.

Supplementary Partial European Search Report of the European Patent Office dated Nov. 22, 2016 and mailed on Dec. 2, 2016 of European Patent Application No. EP 11 84 5027 filed on Nov. 30, 2011.

Supplementary European Search Report dated Apr. 25, 2017 and mailed May 9, 2017 of European Patent Application No. EP 11 84 5027 filed on Nov. 30, 2011.

European Search Report of the European Searching Authority dated Mar. 15, 2016 of European Patent Application No. EP 11 84 5986 filed Nov. 30, 2011.

Olympus Operation Manual, dated 2003, 102 pages, entire document.

Third party submission filed on Jul. 17, 2014 in U.S. Appl. No. 13/989,573, filed Jul. 17, 2013.

Third party submission filed on Jul. 17, 2014 in U.S. Appl. No. 13/989,649, filed Jul. 17, 2013.

International Search Report and Written Opinion by the International Searching Authority Filed in Application No. PCT/US2011/062594 on Nov. 30, 2011 and mailed on Mar. 29, 2012.

International Preliminary Report on Patentability malled Dec. 3, 2020, in International Application No. PCT/US2019/030888 filed May 6, 2019.

International Search Report and Written Opinion mailed Sep. 5, 2019, in International Application No. PCT/US2019/030888 filed May 6, 2019.

Olympus Medical System Corp., "Evis Exera II GIF/CF/PCF Type 180 Series Reprocessing Manual," pp. 1-112, published 2009.

EU-IPO Community Registration Design No. 000279039-0004; Filed Jul. 1, 2005; Owner: Filtertek B.V.; from internet website: https://euipo.europa.eu/eSearch/#basic/1 +1 +1 +1/100+100+100+100/000279039-0004.

Olympus America, Inc., "Endoscope Channel Guide," p. 1 of 1, published 2003.

Olympus Medical Systems Corp., "Olympus Evis Exera GIF/CF/PCF Type 160 Series Operation Manual," pp. 1-102, published 2003.

Olympus Medical Systems Corp., "Olympus Evis Exera II Duodenovideoscope T JF Type Q180V Reprocessing Manual/Instructions," pp. 1-118, published 2015.

Olympus MH-948 Cleaning Adapter Endoscopy, Internet advertisement on Ebay, website visited Jan. 29, 2019; https://www.ebay.com/p/Olympus-Mh-948-Endoscope-AW-Channel-Cleaning-Adapter/9021398174.

* cited by examiner

CLEANING ADAPTER WITH AND WITHOUT SAFETY TAG

PRIORITY CLAIM

This application claims priority to and benefit of U.S. Provisional Application with Ser. No. 62/674,336, filed on May 21, 2018, which is herein incorporated by reference in its entirety.

BACKGROUND

Endoscopes are well-known in the art and are commonly used for numerous medical procedures. A control section of an endoscope may include a suction cylinder, air/water cylinder, and the like. Valves may be inserted into these cylinders to control various functions of the endoscope. After each use, an endoscope will undergo cleaning, disinfection and/or sterilization to prevent the spread of disease, viruses, bacteria, and illness.

One way an endoscope is cleaned is by a technician manually using a cleaning solution, such as, an enzymatic cleaner. The endoscope is then soaked in a high-level disinfectant. Cleaning the endoscope is vital to ensure that the disinfection process is effective. Once manual cleaning is finished, the technician visually inspects the endoscope to make sure that it is clean.

Another way to clean an endoscope is by the use of reusable or non-disposable cleaning adapters, which must also be cleaned, disinfected, and/or sterilized between uses. Unfortunately, there is usually a great expense associated with maintaining a high level of disinfection of the equipment and the reusable cleaning adapter. Reusable cleaning adapters must be carefully tracked together with the corresponding endoscope during cleaning and reprocessing procedures to identify breaches in reprocessing of the endoscope and its corresponding valves, which reduces the risk of cross-contamination among patients when endoscopes and their corresponding valves are reused.

Reusable cleaning adapters are generally made from a combination of metal, plastic and/or rubber and therefore, can be expensive to manufacture.

Thus, there is a need to develop new cleaning adapters that are disposable and methods that reduce or eliminate the need for repeated cleaning, disinfection, and sterilization of the cleaning adapter and reduce or eliminate the risk of infecting the patient when the source of contamination originates from the cleaning adapter. There is also a need to provide users with a low cost cleaning adapter option that eliminates the need to track and reprocess cleaning adapters, which will allow users to save time and effort in the overall endoscope reprocessing cycle.

There is also a need to develop a safety tag that attaches to a cleaning adapter to prevent a user from confusing the cleaning adapter with an air/water valve and improperly using the cleaning adapter instead of an air/water valve during an endoscope procedure.

SUMMARY

New devices and methods are provided that reduce or eliminate the need for repeated cleaning, disinfection, and sterilization of cleaning adapters, as well as reduce the risk of infecting a patient when the patient undergoes an endoscopic procedure. Devices and methods are further provided that are disposable, thereby providing users with a low cost cleaning adapter option that eliminates the need to track and reprocess cleaning adapters. In some embodiments, because the cleaning adapter is disposable and for single use, the cleaning adapter can be discarded after single use and there is no risk of contaminating the next patient where the source of contamination is from the cleaning adapter. New devices and methods are also provided that prevent a user from using the wrong valves during the course of an endoscope procedure.

In some embodiments, a cleaning adapter for an endoscope is provided. The cleaning adapter comprises a main stem comprising a first through hole extending transversely through the main stem, a second through hole extending transversely through the main stem, and a channel within the main stem fluidly coupling the first through hole to the second through hole.

In some embodiments, a disposable cleaning adapter for an endoscope is provided. The cleaning adapter comprises a main stem comprising a distal end defining a counterbore, a first through hole extending transversely through the main stem, and a second through hole extending transversely through the main stem. A channel is provided that is configured to fluidly couple the first through hole to the second through hole, and the disposable cleaning adapter comprises a plug disposed in the counterbore.

In some embodiments, a method of cleaning an endoscope is provided. The method comprises removing an air/water valve from air/water cylinder of an endoscope; inserting a portion of a main stem of a cleaning adapter into the air/water cylinder of the endoscope, the cleaning adapter comprising the main stem comprising a distal end defining a counterbore, a first through hole extending transversely through the main stem, a second through hole extending transversely through the main stem, and a channel configured to fluidly couple the first through hole to the second through hole, and a plug disposed in the counterbore; and directing water into the first through hole and the second through hole of the cleaning adapter and through the air/water cylinder of the endoscope to clean the endoscope.

In some embodiments, a kit for cleaning an endoscope is provided. The kit comprises a cleaning adapter comprising a main stem comprising a distal end defining a counterbore, a first through hole extending transversely through the main stem, a second through hole extending transversely through the main stem, and a channel configured to fluidly couple the first through hole to the second through hole, and a plug disposed in the counterbore; and instructions for cleaning the endoscope.

In some embodiments, a method for manufacturing a cleaning adapter for an endoscope is provided. The method comprises molding or 3D printing a main stem, the main stem comprising a first through hole extending transversely through the main stem, a second through hole extending transversely through the main stem, and a channel within the main stem fluidly coupling the first through hole to the second through hole; attaching a retainer ring to the main stem; attaching a resilient member to the retainer ring; and attaching a button cap to the main stem.

In some embodiments, a method for manufacturing a cleaning adapter for an endoscope is provided. The method comprises molding or 3D printing a main stem, the main stem comprising a first through hole extending transversely through the main stem, a second through hole extending transversely through the main stem, and a channel within the main stem fluidly coupling the first through hole to the second through hole; attaching a retainer ring to the main stem; and attaching a resilient member to the retainer ring.

In some embodiments, a tag for an endoscope valve is provided. The tag comprises a planar surface having an opening configured to receive a region of the endoscope valve. A perforation is disposed adjacent to and contacting the opening and the perforation is configured to engage the region of the endoscope valve. A fold line is disposed adjacent to the opening and extends perpendicular to an edge of the planar surface.

In some embodiments, a tag for an endoscope valve is provided. The tag comprises a planar surface having an opening configured to receive a region of the endoscope valve. A perforation is disposed adjacent to and contacting the opening. The perforation is configured to engage the region of the endoscope valve. A first fold line is disposed adjacent to the opening and extends perpendicular to an edge of the planar surface and a second fold line contacts the first fold line.

In some embodiments, a method of cleaning an endoscope is provided. The method comprises removing a tag from a cleaning adapter, the tag comprising a planar surface having an opening receiving a region of the cleaning adapter; a perforation disposed adjacent to and contacting the opening, the perforation engaging the region of the endoscope valve; and a fold line disposed adjacent to the opening and extending perpendicular to an edge of the planar surface.

In some embodiments, a kit for an endoscope is provided. The kit comprises a tray having a compartment receiving a cleaning adapter, the cleaning adapter engaging a tag. The tag comprises a planar surface having an opening receiving a region of the cleaning adapter. A perforation is disposed adjacent to and contacting the opening and the perforation engages the region of the cleaning adapter. A fold line is disposed adjacent to the opening and extending perpendicular to an edge of the planar surface.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
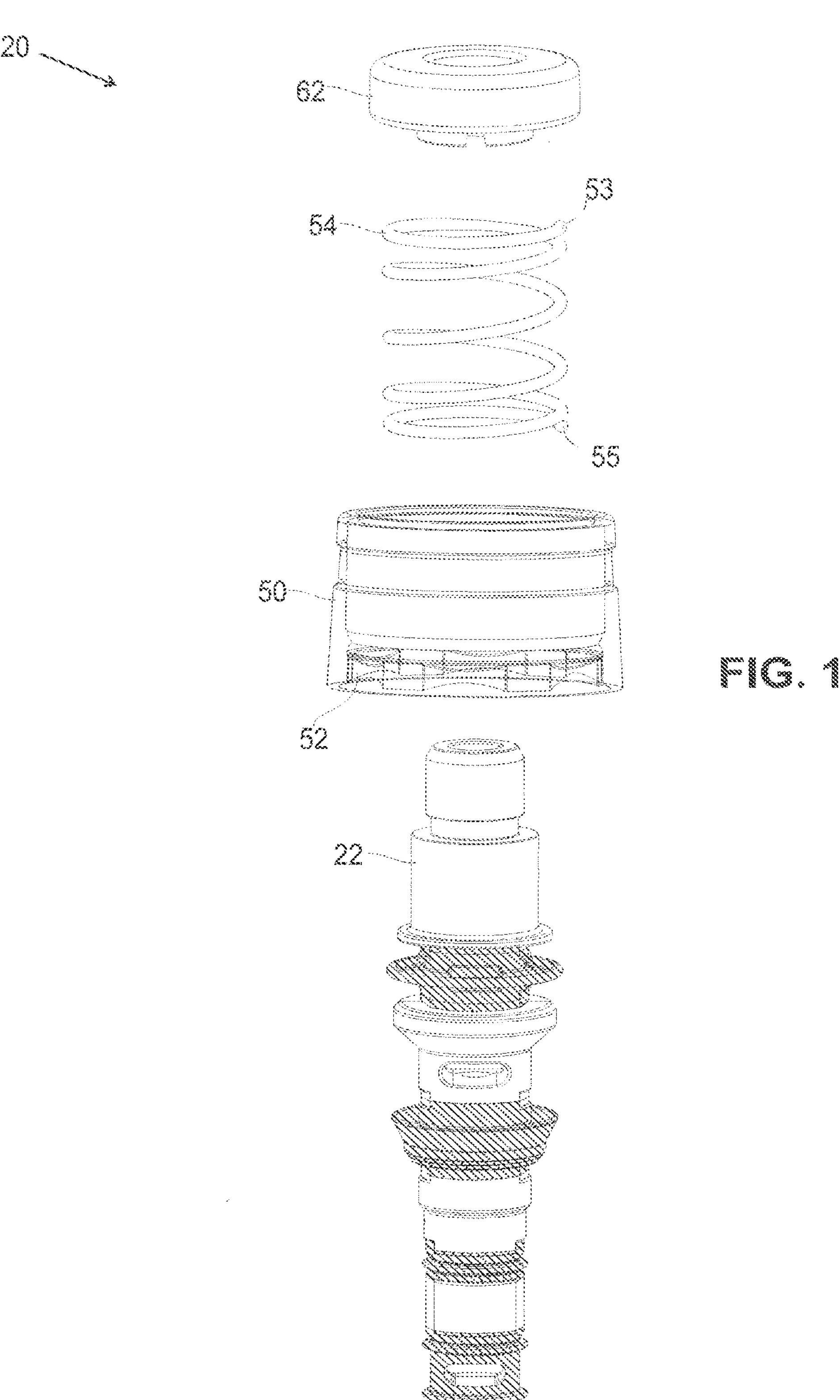
FIG. 1 illustrates a perspective exploded view of components of an embodiment of a cleaning adapter.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

It is noted that, as used in this specification and the appended claims, the singular forms "a," "an," and "the," include plural referents unless expressly and unequivocally limited to one referent. Thus, for example, reference to "a seal" includes one, two, three or more seals.

We refer now to the drawings wherein depicted elements are not necessarily shown to scale and wherein like or similar elements are designated by the same reference numeral through the several views.

Referring to the drawings in general, it will be understood that the illustrations are for the purpose of describing particular embodiments of the disclosure and are not intended to be limiting thereto.

While most of the terms used herein will be recognizable to those of ordinary skill in the art, it should be understood that when not explicitly defined, terms should be interpreted as adopting a meaning presently accepted by those of ordinary skill in the art.

In some embodiments, a disposable cleaning adapter is provided that is manufactured as a single use fluid flow control valve. The cleaning adapter is used for pre-cleaning of the internal air/water channels of a gastrointestinal (GI) endoscope. The cleaning adapter can be installed into or onto the air/water cylinder or port of the GI endoscope and allows the user to switch between two flow modes. In some embodiments, the air/water cylinder contacts and intersects with the air and water channels of the endoscope. The first flow mode is the air-only flow mode or uncompressed configuration (shown in FIG. 12). In this mode, the cleaning adapter directs airflow through a first through hole and a second through hole of the cleaning adapter in order to help purge fluids. The second mode is the water-only flow mode or compressed configuration (shown in FIG. 13), where the user compresses the resilient member (e.g., spring) by pressing the button cap in a downward direction toward the boot. In this mode, the cleaning adapter directs fluid, such as water, through one or more of the through holes to facilitate rinsing of the endoscope channels and removes debris from the channel (e.g., such as bodily fluids, fecal matter, tissue, etc.). The cleaning adapter will allow fluid to flow in a distal direction and prevents backflow into the endoscope's umbilicus section.

In some embodiments, the cleaning adapter comprises a rigid, cylindrical valve main stem with flexible over-molded seal features. The cleaning adapter is assembled with a boot, resilient member, such as a spring, and a button-head cap. The main stem includes a first through hole and a second through hole connected by an internal axial channel that serves as the fluid path through the cleaning adapter. In some embodiments, the internal axial channel extends through a distal end of the rigid main stem where it, for example, can be plugged by an over-molded flexible material, creating the end of the fluid path.

In some embodiments, the design of the cleaning adapter provides a business manufacturing advantage. For example, the cleaning adapter can be produced in high volumes via injection molding without the need for machining processes such as turning or drilling. Further, the plug design at the distal end of the main stem provides a technical manufacturing advantage in that it allows the internal axial channel to be created using a short and stable core pin that extends through the distal end of the main stem as opposed to a longer, more unstable pin extending through the top which would be prone to deflection or bending due to the high plastic pressures during the injection molding process.

In some embodiments, the cleaning adapter provides a user with a low cost option that is compatible with GI endoscopes. The cleaning adapter also eliminates the need for reprocessing and tracking of reusable cleaning adapters which allows a user to save time and effort in the overall endoscope reprocessing cycle. In some embodiments, the cleaning adapter is made at a low cost, is disposable after a single use and is able to be produced in high volumes or mass quantities.

In some embodiments, the form and geometry of the over-molded seals of the cleaning adapter can be modified in order to optimize and balance seal performance against frictional forces during use. The seals can be tested for seal integrity, allowable fluid flow rates, and human use factors such as mechanical force required to install, remove, and actuate the disposable cleaning adapter.

In some embodiments, a tag is provided that can be assembled onto a cleaning adapter. The tag acts as a physical barrier to prevent use until the tag is torn off the cleaning adapter. In some embodiments, a warning in the form of a text and/or a symbol can be printed on the tag. In some embodiments, the tag can be a color, such as, for example, orange. In some embodiments, the tag can be made from a thick material to prevent the cleaning adapter from fully seating in a port of an endoscope if the tag is not removed before use. In some embodiments, the tag can be made from a material that does not create debris, particulate or tear during assembly, such as, for example, polyethylene. In some embodiments, the tag can be made from polypropylene or chipboard. In some embodiments, the tag is made from a material that does not hinder the effectiveness of an ethylene oxide (ETO) sterilization process and does not degrade/warp during sterilization, transport or storage (e.g., for up to a three-year shelf life).

Cleaning Adapter

Referring to FIGS. 1-9, a cleaning adapter 20 is provided that is configured for pre-cleaning or cleaning of the internal air/water channels of a gastrointestinal (GI) endoscope. The cleaning adapter is compatible with various brands of endoscopes, such as, for example, Olympus®, Pentax®, FujiFilm™, or the like. The cleaning adapter can be installed into the air/water cylinder or port of the GI endoscope and allows a user to switch between two flow modes, as described herein. In some embodiments, the cleaning adapter is disposable and is intended as a single use cleaning adapter.

The cleaning adapter includes a main stem 22 comprising a proximal end 24, a distal end 26, and a longitudinal axis a disposed therebetween. The main stem can be monolithic and has a length L1. The length L1 of the main stem can be from about 4 cm to about 6 cm. The main stem can be injection molded, sonic welded, machined or 3D printed, as described herein.

The main stem includes a first through hole 28 that extends transversely through the main stem. The first through hole has an axis b that is transverse relative to longitudinal axis a. A second through hole 30 extends transversely through the main stem and can be substantially parallel to the first through hole. The second through hole has an axis c that is transverse relative to longitudinal axis a and parallel relative to axis b. The first through hole and the second through hole can be configured such that they are slot shaped. The through holes can also be round, oval, and/or rectangular. The through holes can be the same or a different size and can be from about 1 mm to about 4 mm. The second through hole includes a first portion and a second portion, where the first portion is larger than the second portion. The first portion remains open after overmolding and allows water and air to flow during use. The second portion is employed during manufacturing and allows flow of a material, such as, a plastic resin for the creation of a plug 42, as described herein, during overmolding. The second portion can close as a result of the overmolding process.

A channel 32 is disposed within the main stem and fluidly couples the first through hole to the second through hole such that the channel serves as a fluid path for air and water through the main stem of the cleaning adapter. The channel is an internal axial channel and extends along longitudinal axis a. The channel has a length L2 and a width W1. Length L2 can be from about 0.5 cm to about 2 cm and W1 can be from about 0.1 cm to about 0.3 cm.

At the proximal end of the main stem, an opening 34 extends along longitudinal axis a of the main stem. The opening is the entrance to a channel 36. Channel 32 is not connected to channel 36. The distal end of the main stem comprises an opening 38. The opening includes a counterbore 40 and a plug 42 is disposed within the counterbore. The plug is configured to terminate the fluid path that is made by the first through hole, the second through hole and channel 32.

Figure 2:
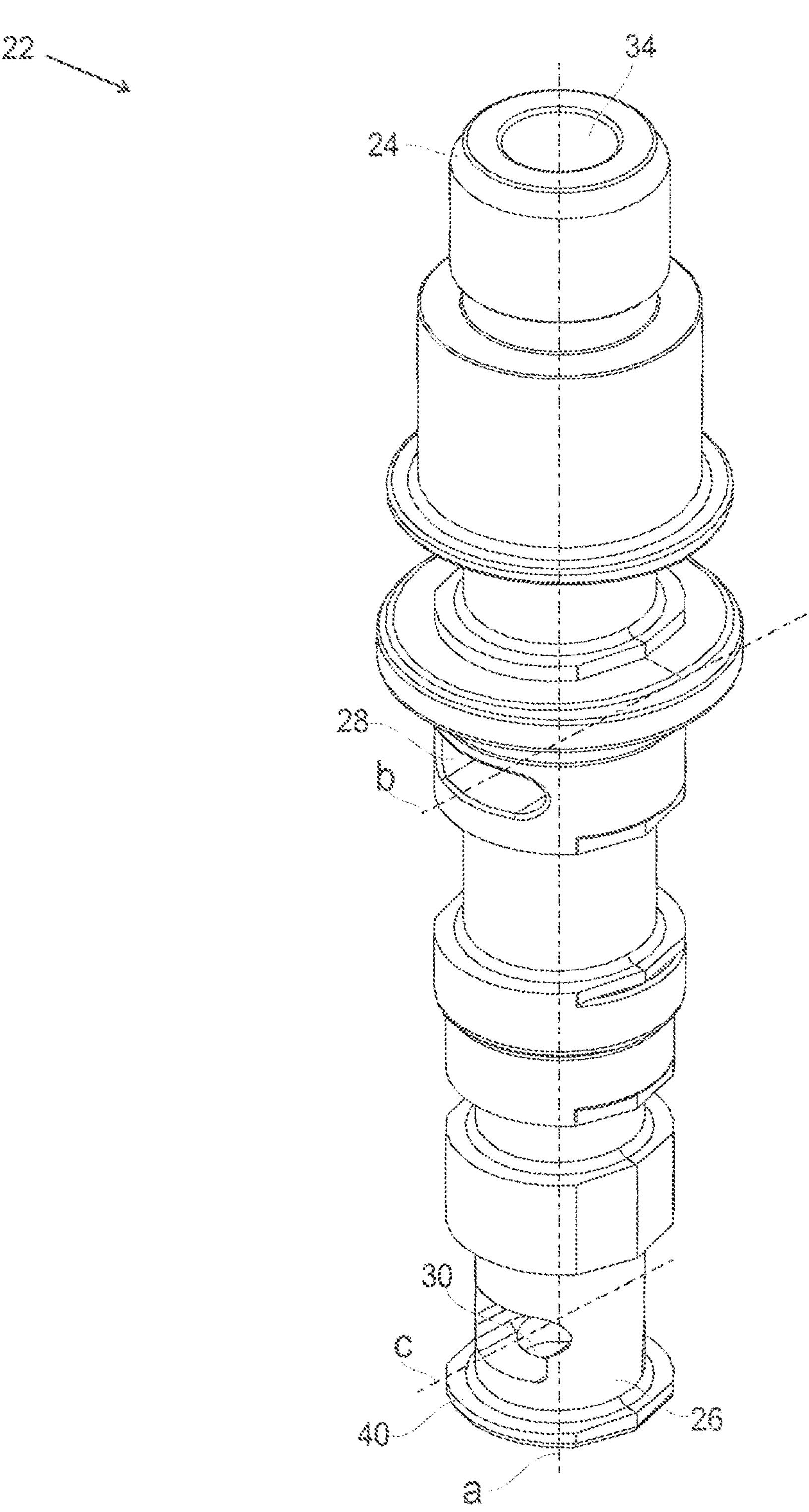
FIG. 2 illustrates a perspective view of an embodiment of the main stem of the cleaning adapter of FIG. 1 shown without one or more gaskets.

The main stem can comprise one or more ridges 44 and grooves 46, or a plurality of ridges and grooves. The ridges and grooves are disposed circumferentially about the main stem and can be monolithic with the main stem. These ridges and/or grooves can be rigid or they can be flexible. In some embodiments, the ridges and grooves are not monolithic with the main stem, as shown in FIG. 2.

Figure 3:
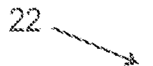
FIG. 3 illustrates a front view of an embodiment of the main stem of the cleaning adapter of FIG. 1.
Figure 3:
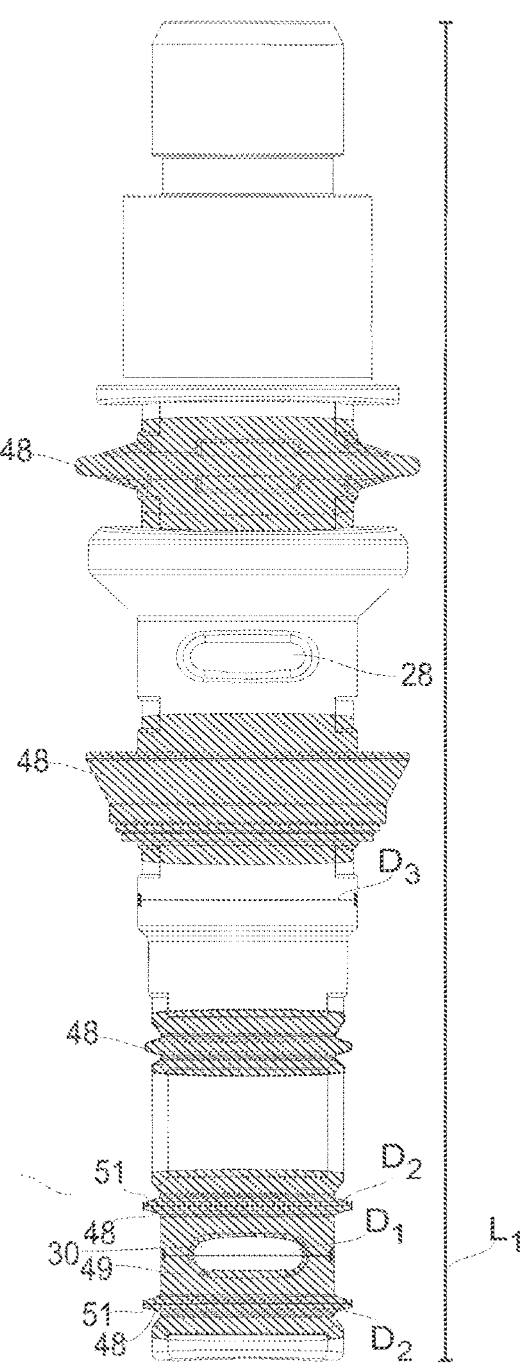
Figure 4:
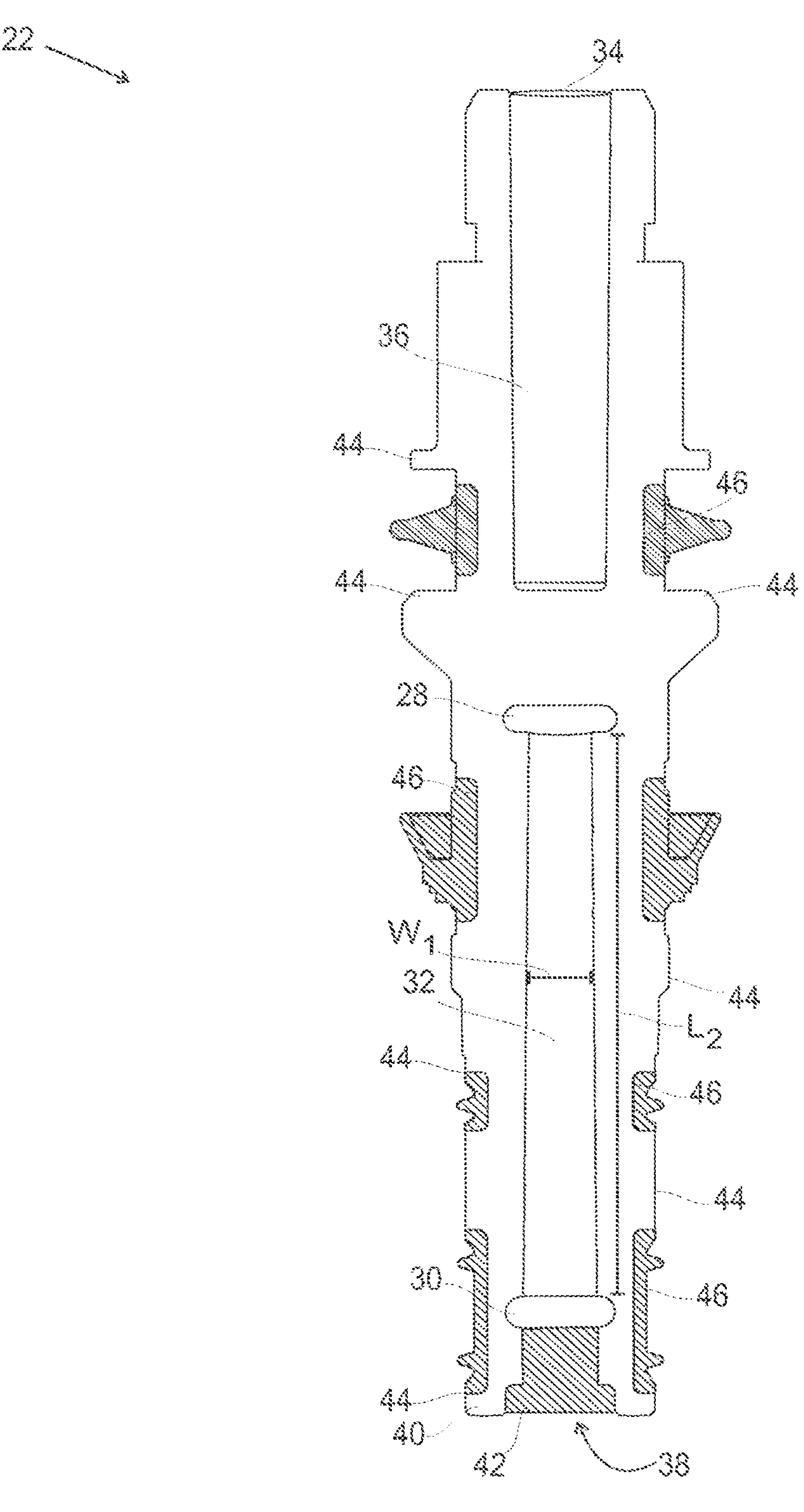
FIG. 4 illustrates a cross sectional front view of an embodiment of the main stem of the cleaning adapter of FIG. 1.

One or more gaskets 48 or a plurality of gaskets are disposed in the plurality of grooves described above. The one or more gaskets or the plurality of gaskets are configured to reduce friction when the cleaning adapter is disposed within the air/water cylinder of a GI endoscope. The one or more gaskets or the plurality of gaskets can comprise four gaskets disposed in four of the plurality of grooves of the main stem, as shown in FIG. 3. In some embodiments, at least one gasket or more is over-molded onto the main stem. The four gaskets can comprise a wiper seal, an umbrella gasket and sealing rings located from the proximal end to the distal end of the main stem. The umbrella gasket is disposed distal to the first through hole, as shown in FIG. 3. In some embodiments, the one or more gaskets or the plurality of gaskets provide a sealing function. For example, air and water flow is either blocked or directed into the through holes and the air and water channels of the endoscope due to the position and size/geometry of the one or more gaskets or the plurality of gaskets which form radial seals via their mechanical interference against the surfaces of the air/water cylinder at specific points. In some embodiments, the umbrella gasket has a thick annular base that functions as a sealing ring in the compressed position, as described herein. In the uncompressed position, as described herein, a thin umbrella shaped membrane of the umbrella gasket folds radially inward and away from the walls of the air/water cylinder to allow air to flow around the membrane in the proximal direction of the main stem, but may fold radially outward toward the walls to prevent backflow of fluids in the reverse direction.

In some embodiments, a body 49 is disposed about the second through hole and includes a plurality of gaskets 48, such as a plurality of sealing rings 51. The body has a first diameter D1, and the plurality of sealing rings have a second diameter D2, as shown in FIG. 3. In some embodiments, diameter D1 is about 0.204 inches and diameter D2 is about 0.241 inches. In some embodiments, the main stem has a diameter D3, and diameter D3 can be equal to diameter D2. In some embodiments, diameter D1 is less than diameters D2 and D3 so that greater flexibility of the gaskets in their sealing function is facilitated.

In some embodiments, the one or more gaskets or the plurality of gaskets are interconnected and monolithic with each other, forming a single body. In some embodiments, the one or more gaskets or the plurality of gaskets are over-molded or are molded separately onto the main stem, as described herein. Over-molding the gaskets on the main stem avoids the need to slide the one or more gaskets or the plurality of gaskets onto the main stem, which may tear or damage the gaskets during assembly. Over-molding the one or more gaskets or the plurality of gaskets onto the main stem also avoids the need to separate the main stem into several components, which significantly reduces the number of components and assembly steps.

In some embodiments, the one or more gaskets or the plurality of gaskets can alternatively be secured to the main stem by threading, welding, chemical bonding, mechanical grip, staking or via a suitable adhesive.

The cleaning adapter further comprises a boot 50 disposed about a retainer ring 52, as shown in FIGS. 1 and 7-9. The retainer ring is disposed about the main stem at the proximal end, and a resilient member 54 contacts an inner surface of the retainer ring. The resilient member can be a spring having a certain thickness and length. A resilient member can further include, for example, a plastic, rubber or other elastic member that maintains its original shape or position after being compressed. The resilient member can have a proximal portion 53 and a distal portion 55.

Figure 7:
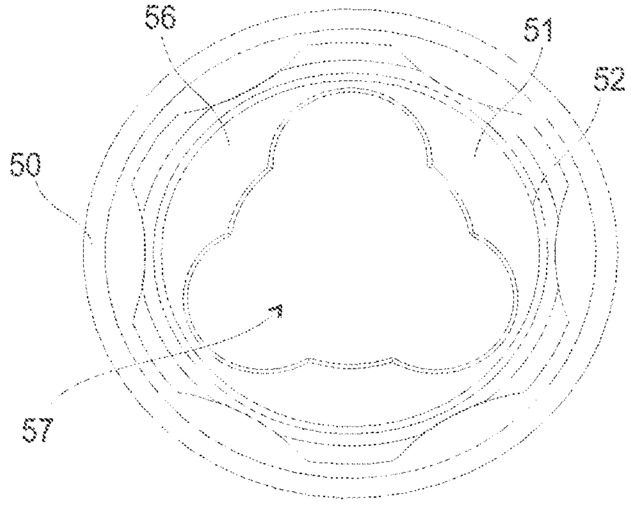
FIG. 7 illustrates a bottom view of an embodiment of a retainer ring and a boot of the cleaning adapter of FIG. 1.
Figure 8:
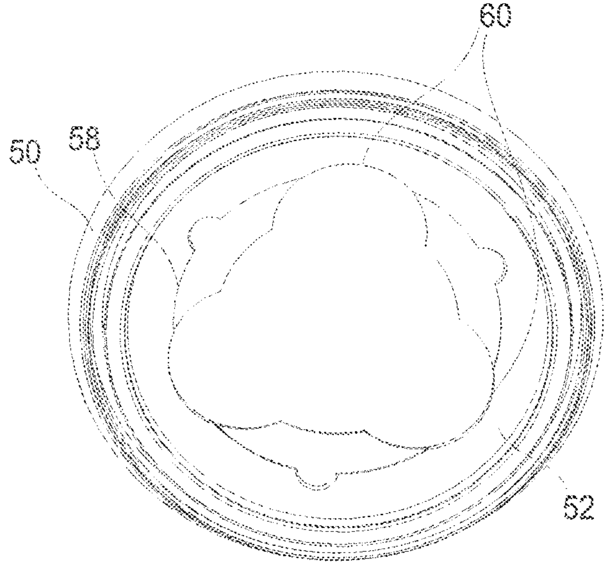
FIG. 8 illustrates a top view of an embodiment of a retainer ring and a boot shown in FIG. 7.
Figure 9:
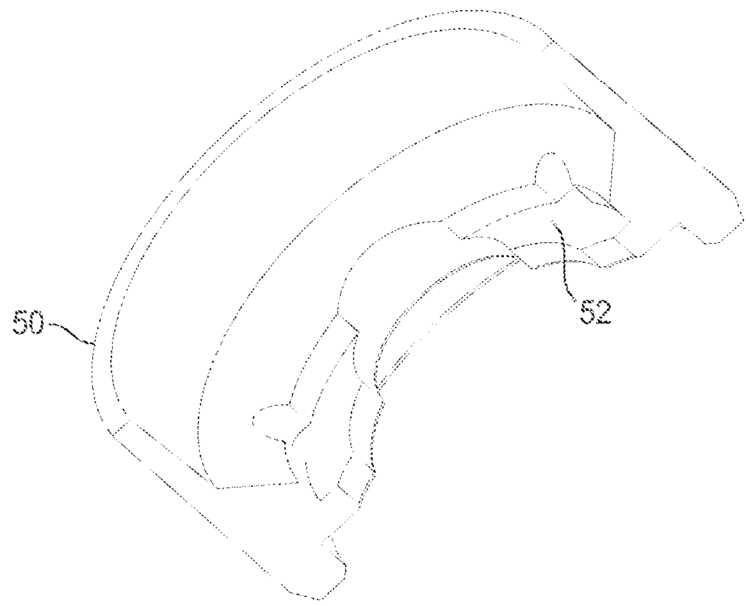
FIG. 9 illustrates a cross sectional perspective view of a retainer ring of the cleaning adapter of FIG. 1.

The retainer ring comprises a partition 56, as shown in FIGS. 7 and 8 that includes an opening 57 for receiving the proximal end of the main stem. The opening includes a circumferential edge 58 that defines a cutout 60. The cutout can have various geometrical designs. While the opening is shaped as a larger diameter circle with three semi-circular cutouts along the radius of the larger diameter circle, it should be recognized that any other suitably shaped opening may be utilized (e.g. square, triangle, etc.).

A button cap 62 is attached to the proximal end of the main stem or is monolithic with the proximal end of the main stem. The resilient member is configured to contact the retainer ring and the button cap, and movement of the button cap in a downward direction toward the retainer ring compresses the resilient member in a downward position relative to the retainer ring. In some embodiments, the distal portion 55 of the resilient member rests on a surface 51 of the retainer ring (e.g., spring cup or spring stanchion) and the proximal portion 53 of the resilient member rests on a surface 63 of the button cap 62. This occurs, for example, when the resilient member is in a compressed configuration and an uncompressed configuration shown in FIGS. 12 and 13. In some embodiments, the button cap can be monolithic with the main stem.

The outside diameter of a top end of the button cap is larger than the diameter of the resilient member, and the inside diameter of the opening in the partition is smaller than the diameter of the resilient member to retain the resilient member between the retainer ring and the button cap.

Figure 5:
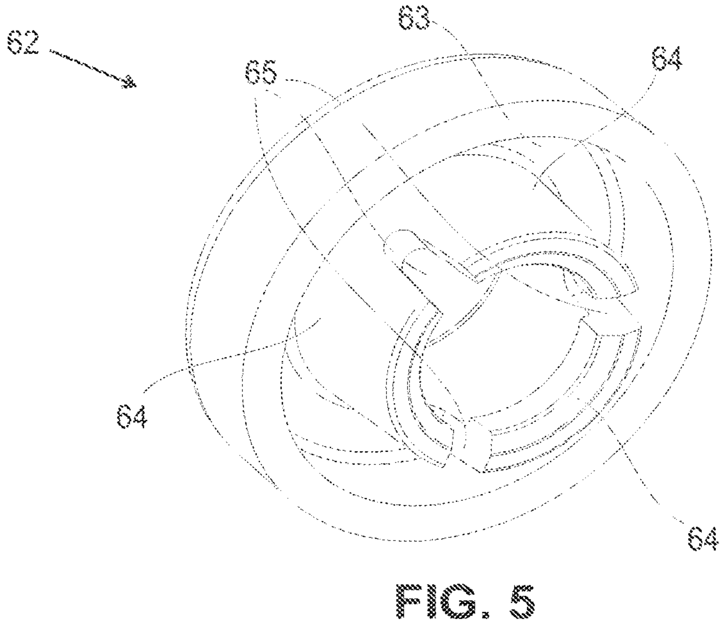
FIG. 5 illustrates a perspective view of an embodiment of a button cap of the cleaning adapter of FIG. 1.
Figure 6:
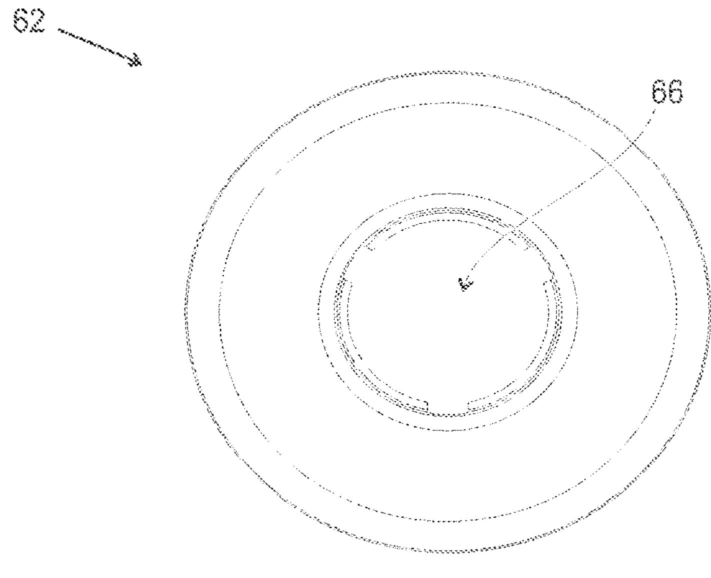
FIG. 6 illustrates a top view of an embodiment of a button cap of FIG. 5.

The button cap can be a snap fitting or an interference fitting and engages the proximal end of the main stem, as shown in FIGS. 5 and 6. The button cap can include projections 64 and/or recesses 65 when the button cap is in a snap fitting or interference fitting engagement with the proximal end of the main stem. The button cap can have 2, 3, 4, 5 or 6 projections. The button cap may include an opening 66 that is in communication with the opening at the proximal end of the main stem, as described above. Alternatively, the main stem may be secured to the button cap using ultrasonic welding, a suitable adhesive, mechanical attachment (e.g. threading or the like) or any suitable attachment method.

Figures 12, 13:
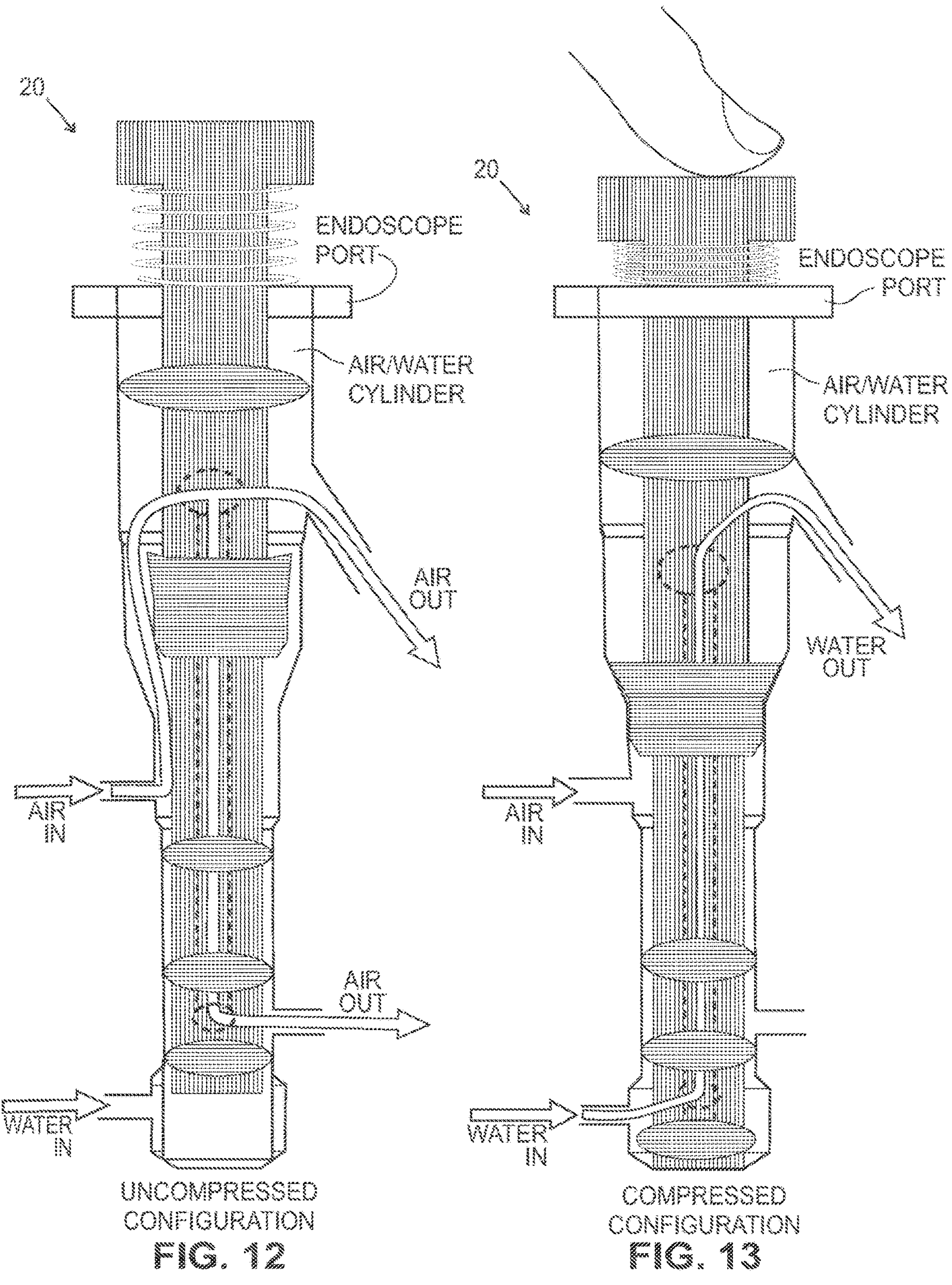
FIG. 12 illustrates air and water flow in and out of the cleaning adapter when the cleaning adapter is in an uncompressed configuration in the endoscope air/water cylinder.
FIG. 13 illustrates air and water flow in and out of the cleaning adapter when the cleaning adapter is in a compressed configuration in the endoscope air/water cylinder.

The cleaning adapter can be installed into the air/water port or cylinder of a GI endoscope and the cleaning adapter allows a user to switch between two flow modes, as shown in FIGS. 12 and 13. The first flow mode is the air-only flow mode or the uncompressed configuration, as shown in FIG. 12. In this mode, the button cap is undepressed by the user and the cleaning adapter directs airflow around the umbrella membrane of the umbrella gasket, through the first through hole and the second through hole, and into the air and water channels of the endoscope, in order to facilitate the purging of fluids. In this mode, air and water are taken into the air/water cylinder but water flow is blocked by the cleaning adapter. In the uncompressed configuration, the resilient member is expanded and allows the distance between the button cap to the retainer ring to be at the greatest distance. In some embodiments, in the uncompressed configuration, in the case where a fluid pressure gradient exists in the reverse direction (toward the distal end of the main stem), the umbrella membrane may also prevent backflow of fluids into the umbilicus section of the endoscope.

The second mode is the water-only flow mode or the compressed configuration, as shown in FIG. 13. When the button cap is depressed by the user using the finger or thumb, the resilient member which contacts the underside or surface of the cap via its proximal portion 53 and also contacts an inner surface of the retainer ring via its distal portion 55, the resilient member is compressed causing the button cap to move towards the retainer ring. When the resilient member is compressed, energy is stored in the resilient member. Because the main stem is secured to the button cap, the main stem also moves when the button cap is depressed, thereby allowing the main stem to move into alignment within a desired portion of the air/water cylinder or port of the endoscope. In this mode, the cleaning adapter directs water through one or more of the through holes to facilitate rinsing of the endoscope channels and removes debris, bodily fluid, etc. from the channels of the endoscope.

When the user releases the button cap, the energy stored from the resilient member causes the resilient member to revert back to its uncompressed state and the cleaning adapter returns back to the first flow mode or uncompressed configuration. The resilient member forces the button cap away from retainer ring, which causes the retainer ring to move along the proximal end of the main stem. However, the opening in the partition of the retainer ring is smaller than the diameter of the main stem just above one of the plurality of gaskets or one of the one or more gaskets (e.g., a wiper seal), thereby preventing the retainer ring from advancing beyond the one of the plurality of gaskets or one of the one or more gaskets on the main stem.

It will be understood by one of ordinary skill in the art that at least a portion of the main stem is inserted into at least a portion of the air/water/cylinder of the endoscope. The button cap, resilient member, retainer ring (e.g., spring stanchion) and boot are adjacent to the air/water cylinder so that the user can control the flow of air and water by depressing or releasing the button cap of the cleaning adapter.

Figure 10:
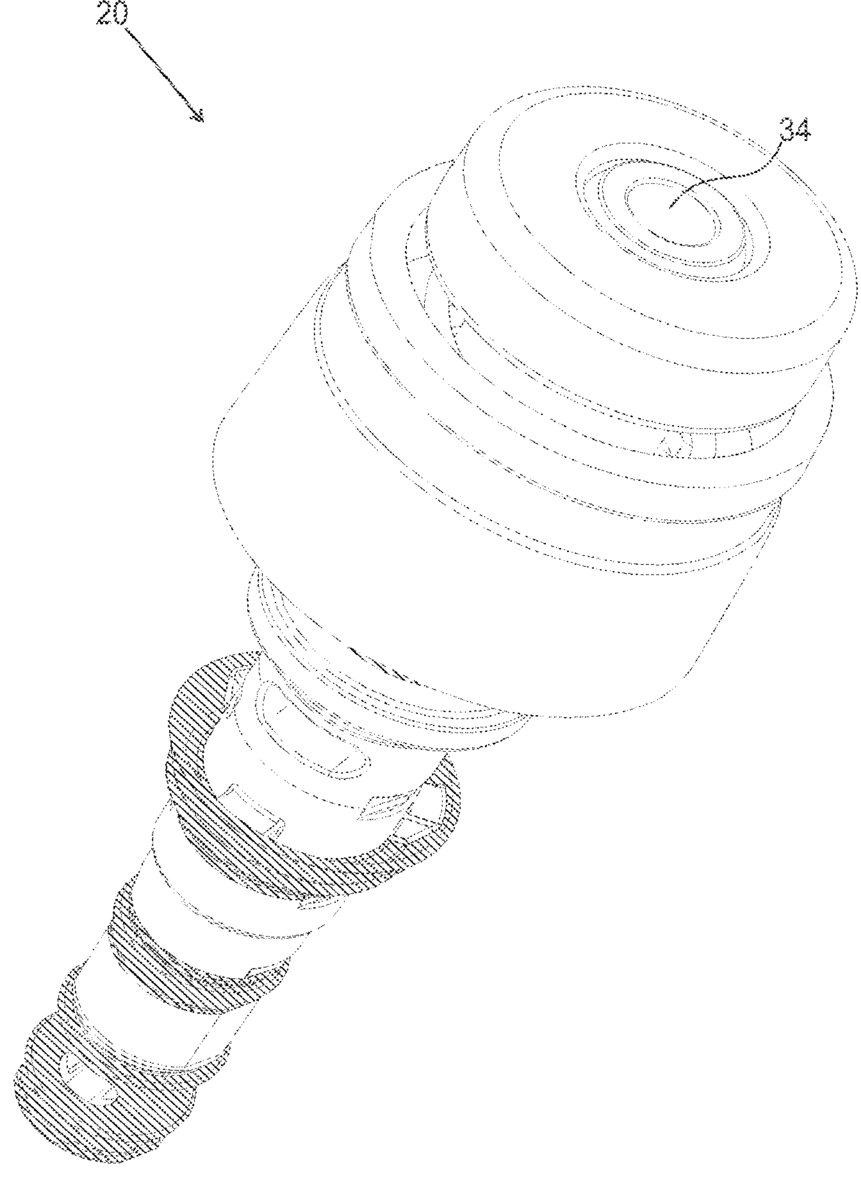
FIG. 10 illustrates a perspective view of an assembled embodiment of a cleaning adapter similar to the cleaning adapter of FIG. 1.
Figure 11:
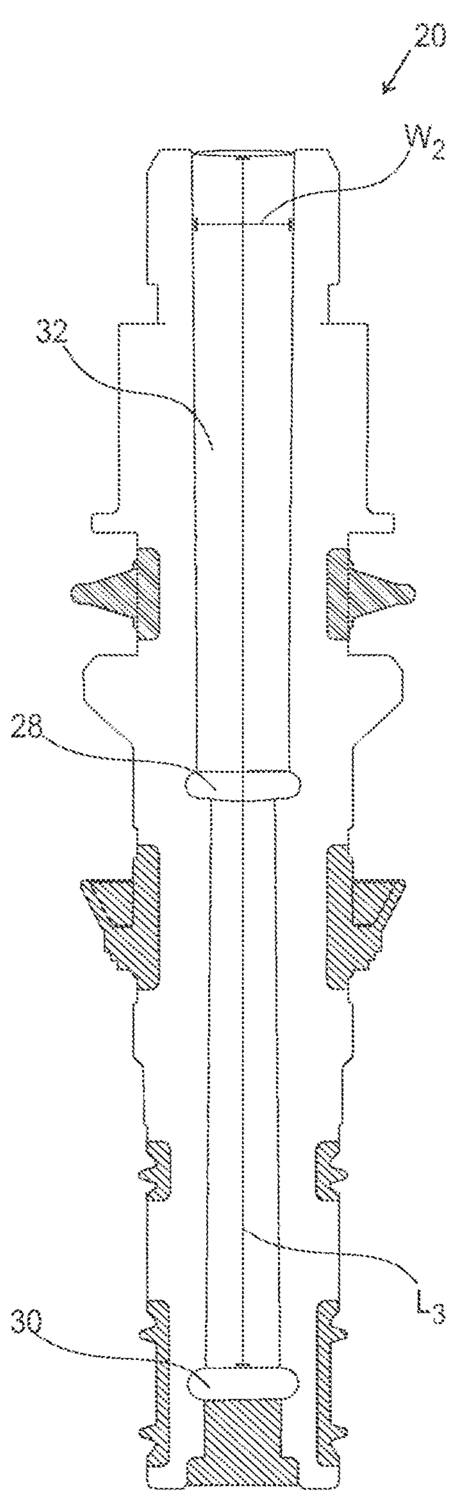
FIG. 11 illustrates a cross sectional side view of an embodiment of the main stem of the cleaning adapter of FIG. 10.

In some embodiments, as shown in FIGS. 10 and 11, cleaning adapter 20 is modified such that channel 32 extends from the proximal end to the distal end of the cleaning adapter. In this embodiment, there is no second channel 36. The channel has a length L3 and a width W2. Length L3 can be from about 0.5 cm to about 4 cm and W2 can be from about 0.1 cm to about 0.6 cm. Width W2 of the channel can vary depending on its location on the channel. The channel, as described above, fluidly couples the first through hole to the second through hole such that the channel serves as a fluid path for air and water through the main stem of the cleaning adapter. This embodiment can reduce the chance of harm during use due to user error.

In this embodiment, the channel allows air to escape or vent from the proximal end of the main stem via opening 34 such that there is less air moving through the channels when the user inserts the cleaning adapter into an endoscope.

In some embodiments, a pressure relief valve, not shown, can be positioned within the main stem disposed between the first through hole and the proximal end of the main stem. The pressure relief valve can reduce the chances of too much air going into the endoscope in case of user error.

In some embodiments, the components of the cleaning adapter including the main stem, button cap, retainer ring, gasket, seals, boot, plug, or other components can be made from the same material or different material.

In some embodiments, the main stem, button cap, retainer ring, gasket, seals, boot, plug, or other components of the cleaning adapter can be fabricated from disposable materials suitable for medical applications, including synthetic polymers.

The main stem can comprise a polymeric material. The polymeric material can be thermoplastic and/or is a polycarbonate. For example, the components of the cleaning adapter, individually or collectively, can be fabricated from materials such as machined or injection molded thermoplastics such as polyaryletherketone (PAEK) including polyetheretherketone (PEEK), polyetherketoneketone (PEKK) and polyetherketone (PEK), carbon-PEEK composites, PEEK-BaS04 polymeric rubbers, polyethylene terephthalate (PET), fabric, silicone, polyurethane, silicone-polyurethane copolymers, polymeric rubbers, polyolefin rubbers, semi-rigid and rigid materials, elastomers, rubbers, thermoplastic elastomers, thermoset elastomers, elastomeric composites, polyphenylene, polychloroprene, polyamide, polyetherimide, polyethylene, epoxy, partially resorbable materials, totally resorbable materials, polyglycolide, polytyrosine carbonate, polycaprolactone, silicone based rubber, liquid silicone rubber, High Consistency Rubber, silicon, TPE, Polypropylene, Polycarbonate, ABS or any combination thereof.

The components of the cleaning adapter, individually or collectively, may also be fabricated from a heterogeneous material such as a combination of two or more of the above-described materials. The components of the cleaning adapter may be monolithically formed, and/or integrally connected, as described herein. The cleaning adapter as described herein may be constructed of a suitable biocompatible material to impart various desirable characteristics, such as flexibility, and resilience.

In some embodiments, components of the cleaning adapter can also be made from a suitable material such as for example, polyurethane, polyurea, polyether (amide), PEBA, thermoplastic elastomeric olefin, copolyester, styrenic thermoplastic elastomer, carbon fiber, glass fiber, ceramics, methacrylates, poly (N-isopropylacrylamide), PEO-PPO-PEO (pluronics), plastic (e.g., polycarbonates), ABS, MABS, or the like or combinations thereof.

In some embodiments, any components of the cleaning adapter can be color coded or color matched. Colors can include, but are not limited to orange, black, red, yellow, brown, blue, purple, gray, green, white, pink, or a combination thereof.

The one or more gaskets or the plurality of gaskets or plug can be formed from a suitable material, such as rubber, plastic, silicone, or any of the materials described herein. The retainer ring can be formed from a suitable material, such as metal, plastic, silicon, stainless steel, or any of the materials as described herein.

In some embodiments, the resilient member may be formed from a suitable material, such as metal, polyurethane, polyurea, polyether (amide), PEBA, thermoplastic elastomeric olefin, copolyester, and styrenic thermoplastic elastomer, carbon fiber, glass fiber, ceramics, methacrylates, poly (N-isopropylacrylamide), PEO-PPO-PEO (pluronics), rubber, plastic, or the like or combinations thereof or any of the materials as described herein. It will be understood that any resilient member (e.g., a member that resumes its original shape or position after being compressed) can be used for the resilient member.

The cleaning adapter can be used in conjunction with detergents. For example, types of detergents may include, but are not limited to acidic, neutral, alkaline or enzymatic detergents. Further, one or more disinfectants can be used in conjunction with the detergents. Different types of disinfectants include, but are not limited to low-level disinfectants, medium-level disinfectants and high-level disinfectants. Specific disinfectants include, but are not limited to glutaraldehyde, ortho-phthalaldehyde (OPA), peracetic acid (PAA), hydrogen peroxide, or combinations thereof.

Although the cleaning adapter is designed to be used with an endoscope, it will be understood that other medical instruments can be used with the present cleaning adapter. These instruments include, for example, colonoscopes, gastroscopes, laparoscopes, bronchoscopes, or any medical instruments with a camera or fiber-and-lens optics that requires air and/or water use.

Cleaning Adapter Methods and Kits

Figure 14:
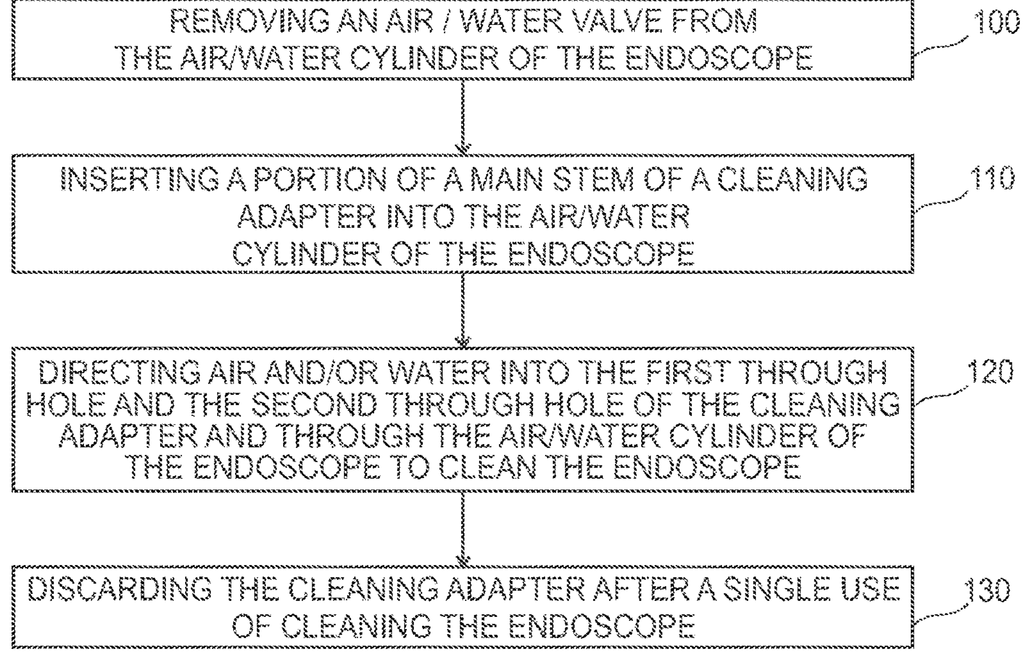
FIG. 14 illustrates a flow diagram of a method of cleaning an endoscope using the cleaning adapter to direct air and water to clean the air and water channels of an endoscope.

A method of cleaning an endoscope is provided and a flow diagram of the method is shown in FIG. 14. The method comprises removing an air and water valve from air/water cylinder of the endoscope, as shown in step 100. The next step 110 is inserting a portion of a main stem of a cleaning adapter into the air/water cylinder of the endoscope. The cleaning adapter, as described above with regard to cleaning adapter 20 comprises the main stem comprising a distal end defining a counterbore, a first through hole extending transversely through the main stem, a second through hole extending transversely through the main stem, and a channel configured to fluidly couple the first through hole to the second through hole, and a plug disposed in the counterbore. The next step 120 is directing air and/or water into the first through hole and the second through hole of the cleaning adapter and through the air/water cylinder of the endoscope to clean, pre-clean and/or flush the endoscope. The main stem of the cleaning adapter is monolithic and comprises a plurality of ridges and grooves disposed circumferentially about the main stem, the plurality of ridges and grooves being monolithic with the main stem. Discarding the cleaning adapter after a single use of cleaning the endoscope is done in step 130.

Figure 15:
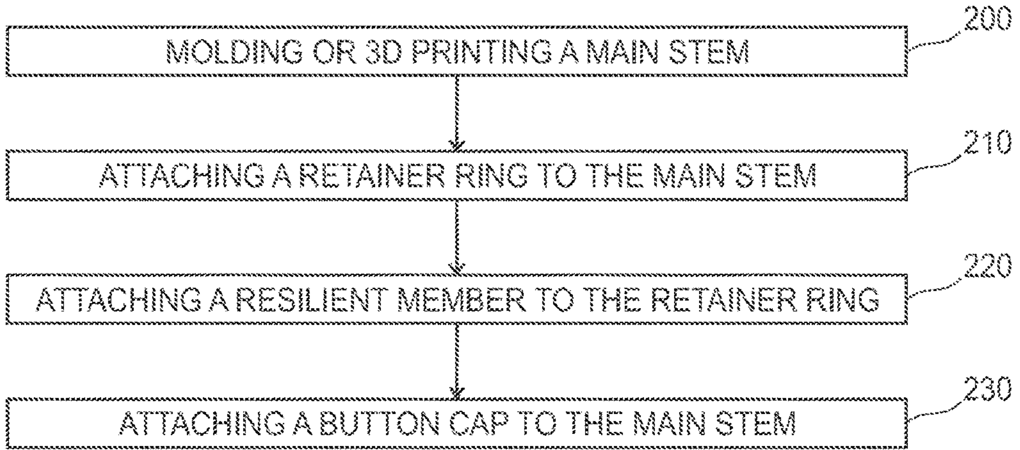
FIG. 15 illustrates a flow diagram of a method of manufacturing a cleaning adapter for an endoscope.

A method for manufacturing a cleaning adapter for an endoscope is provided and a flow diagram of the method is shown in FIG. 15. The method comprises molding or 3D printing a main stem in step 200. The main stem comprises a first through hole extending transversely through the main stem, a second through hole extending transversely through the main stem, and a channel within the main stem fluidly coupling the first through hole to the second through hole. The second step 210 is attaching a retainer ring to the main stem. A third step 220 is attaching a resilient member to the retainer ring. A fourth step 230 is provided for attaching a button cap to the main stem.

In some embodiments, the main stem is color coded and the resilient member is a spring. The button cap is ultrasonically welded to the main stem or can be monolithic with the main stem. The main stem is monolithic and comprises a plurality of ridges and grooves disposed circumferentially about the main stem, and the plurality of ridges and grooves are monolithic with the main stem. A plurality of gaskets are disposed in the plurality of grooves of the main stem and the cleaning adapter is disposable. The cleaning adapter of this method is cleaning adapter 20, as described herein.

Figure 16:
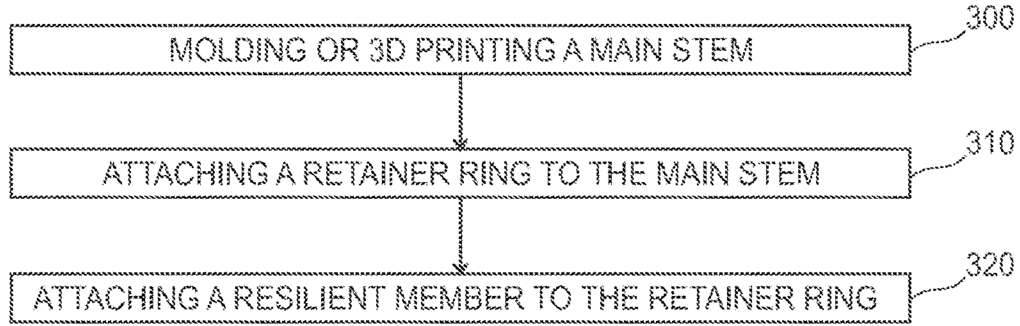
FIG. 16 illustrates a flow diagram of a method of manufacturing a cleaning adapter for an endoscope.

A method for manufacturing a cleaning adapter for an endoscope is provided and a flow diagram of the method is shown in FIG. 16. The method comprises in a first step 300 molding or 3D printing a main stem. The main stem comprises a first through hole extending transversely through the main stem, a second through hole extending transversely through the main stem, and a channel within the main stem fluidly coupling the first through hole to the second through hole. A second step 310 includes attaching a retainer ring to the main stem and a third step 320 includes attaching a resilient member to the retainer ring.

The main stem comprises a button cap that is monolithic with the main stem. The main stem can be monolithic and comprises one or more ridges and one or more grooves disposed circumferentially about the main stem, the one or more ridges and grooves being monolithic with the main stem. One or more gaskets are disposed in the one or more grooves of the main stem. The cleaning adapter of this method is the cleaning adapter 20, as described herein.

In some embodiments, the cleaning adapter and its components can be made by over molding or 3D printing. For example, the main stem can be molded and then the resilient member, retainer ring, gasket, seals, boot, plug and/or button cap can be overmolded on the main stem to make the assembled cleaning adapter. Alternatively, the main stem, button cap, retainer ring, gasket, seals, boot, plug and resilient member can be made by 3D printing. For example, the main stem can be 3D printed and then the resilient member, retainer ring, gasket, seals, boot, plug and/or button cap can be 3D printed on the main stem to make the assembled cleaning adapter.

It will be recognized by one of ordinary skill in the art that numerous steps in the manufacturing process may be optional or may be performed in a different sequence than specifically shown. The scope of the manufacturing process is not limited to the particular sequence and steps discussed herein, except as expressly recited in the claims.

In some embodiments, the cleaning adapter may be made by injection molding, compression molding, blow molding, thermoforming, die pressing, slip casting, electrochemical machining, laser cutting, water-jet machining, electrophoretic deposition, powder injection molding, sand casting, shell mold casting, plaster-mold casting, investment casting, vacuum casting, permanent-mold casting, slush casting, pressure casting, die casting, centrifugal casting, squeeze casting, rolling, forging, swaging, extrusion, shearing, spinning, or combinations thereof.

In some embodiments, the cleaning adapter or one or more of the components of the cleaning adapter may be formed by 3D printing. The terms “three-dimensional printing system,” “three-dimensional printer,” and “printing,” describe various solid freeform fabrication techniques for making three-dimensional articles or objects by selective deposition, jetting, fused deposition modeling, multi-jet modeling, and other additive manufacturing techniques now known in the art or that may be known in the future that use a build material or ink to fabricate three-dimensional objects.

Instructions in the form of schematics encompassing any of the embodiments disclosed herein may be given to a computer to be carried out by a 3D printer. An elastomeric material, such as a silicone-based elastomer may be fed into a reservoir to be used to form the cleaning adapter. In some embodiments, the components of the cleaning adapter may be color coded to signify various physical properties. For example, different colors may be used to differentiate between varying amounts of friction or flexibility between components. Once the material is chosen, an elastomeric material is deposited over a flat fabrication platform one layer at a time. Once a first layer is deposited, a second layer is deposited on top of the first layer. The process is repeated as necessary to create the fitting to the specifications enumerated in the instructions.

Another form of manufacturing the cleaning adapter involves casting the material in a mold. The material can take on the shape of the mold such as, crescent, quadrilateral, rectangular, cylindrical, plug, or any other shape. Additionally, the surface of the mold may be smooth or may include raised features or indentations, for example indentations to create the recesses or notches, to impart features to the cleaning adapter. Features from the mold can be imparted to the cleaning adapter as the material in the mold is dried. In particular aspects, a roughened or friction engaging surface can be formed on the upper surface and/or the lower surface of the cleaning adapter main stem. In some embodiments, protuberances or raised portions can be imparted on the upper surface and/or the lower surface from the mold.

The cleaning adapter may be sterilizable. In various embodiments, one or more components of the cleaning adapter are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the cleaning adapter. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize one or more components of the cleaning adapter, including, but not limited to, gas sterilization, such as, for example, with ethylene oxide or steam sterilization.

Figure 17:
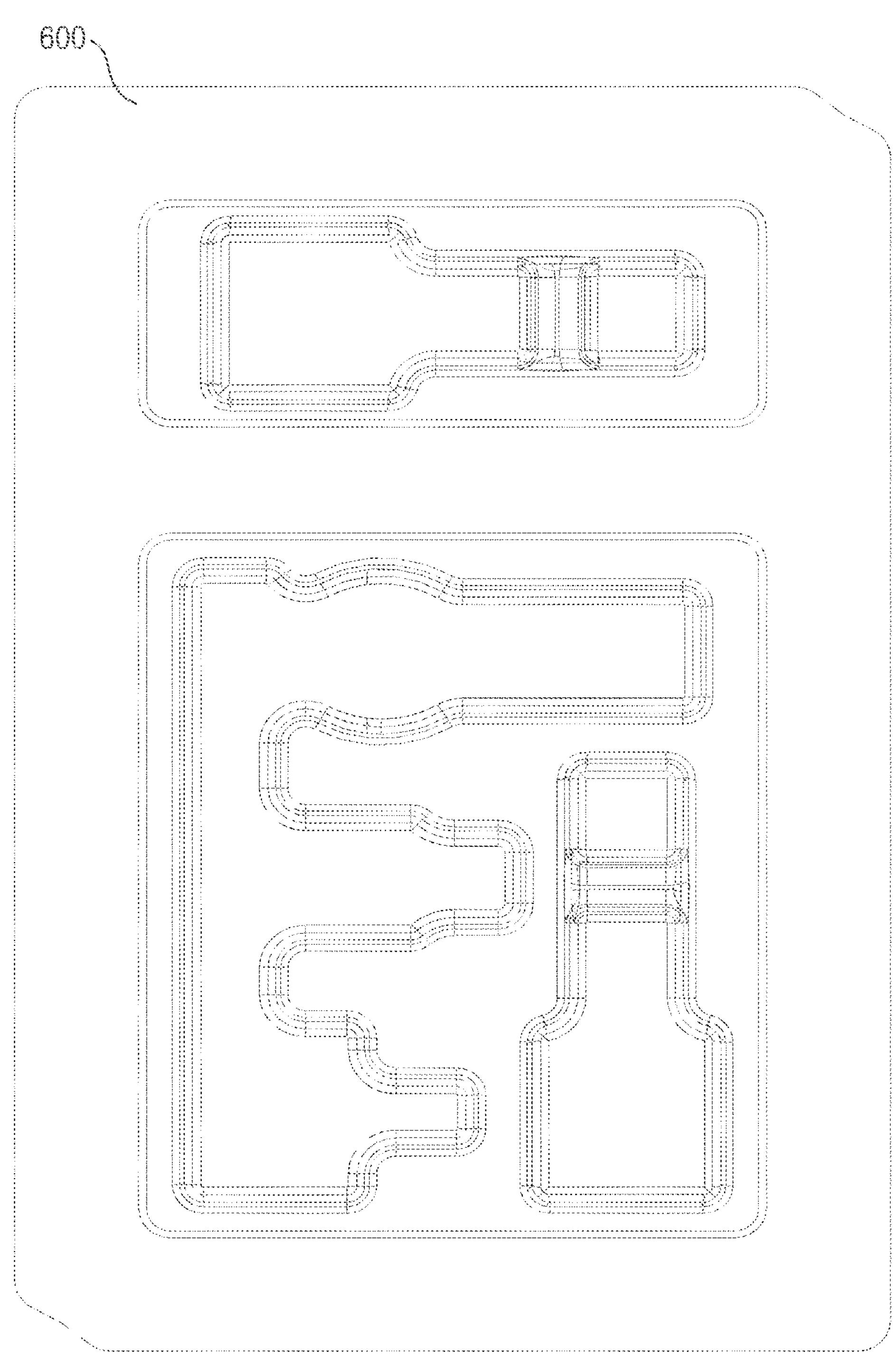
FIG. 17 illustrates a top view of a kit for holding a cleaning adapter for cleaning an endoscope.

In some embodiments, a kit 600 for cleaning an endoscope is provided, as shown in FIG. 17. The kit comprises a cleaning adapter comprising a main stem comprising a distal end defining a counterbore, a first through hole extending transversely through the main stem, a second through hole extending transversely through the main stem, a channel configured to fluidly couple the first through hole to the second through hole, and a plug disposed in the counterbore; and instructions for cleaning the endoscope. The main stem of the cleaning adapter is monolithic and comprises a plurality of ridges and grooves disposed circumferentially about the main stem, the plurality of ridges and grooves being monolithic with the main stem. The cleaning adapter is cleaning adapter 20, as described herein. The kit further includes a disposable air/water valve and a disposable suction valve. Suitable disposable air/water valves and disposable suction valves and/or biopsy valves are available from Medivators Inc. located at 14605 $28^{th}$ Avenue North, Minneapolis, Minnesota 55447 and described in U.S. Pat. Nos. 9,585,545 and 9,408,523. These disclosures are herein incorporated by reference into the present disclosure.

In some embodiments, as an alternative to the instructions for cleaning the endoscope being a part of the kit, as described above, a website can be listed on kit packaging that has instructions for use located on the website.

In various embodiments, a kit is provided that may include additional parts along with the cleaning adapter combined together to be used with the cleaning adapter. The kit may include the cleaning adapter in a first compartment. A second compartment may include one or more containers holding a disinfectant and/or a detergent. A third compartment may include a disposable air/water valve. A fourth compartment may include a disposable suction valve and any other instruments needed for the procedure. A fifth compartment may include gloves, drapes, wound dressings and other procedural supplies for maintaining sterility, as well as an instruction booklet or notification of a website where instructions for using the cleaning adapter can be located. A sixth compartment may include additional cannulas and/or needles. A seventh compartment may include an agent for radiographic imaging. Each device may be separately packaged in a plastic pouch that is radiation sterilized. A cover of the kit may include illustrations of the use of the cleaning adapter and a clear plastic cover may be placed over the compartments to maintain sterility.

Safety Tag

Figure 18:
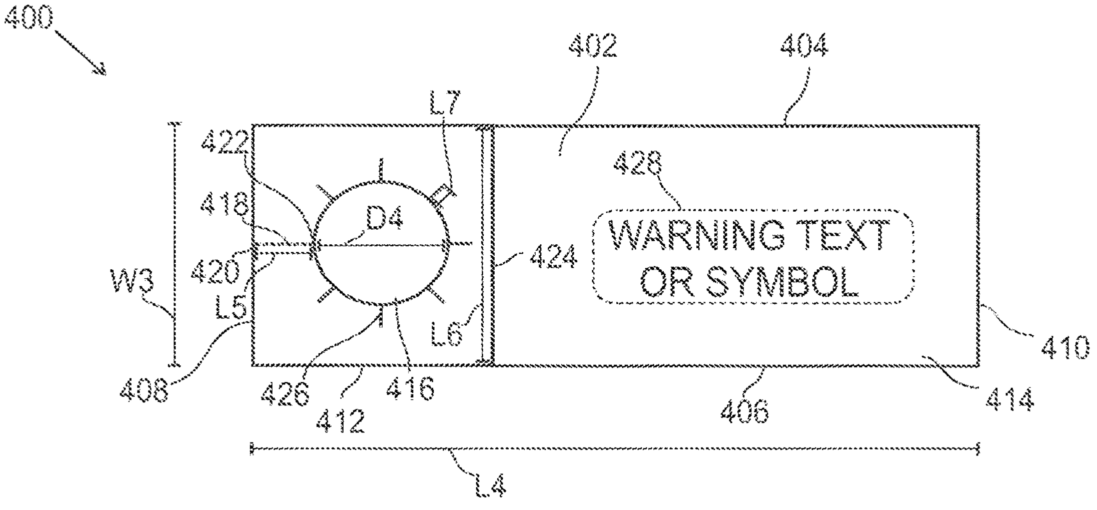
FIG. 18 illustrates a front view of an embodiment of a tag for an endoscope valve.
Figure 19:
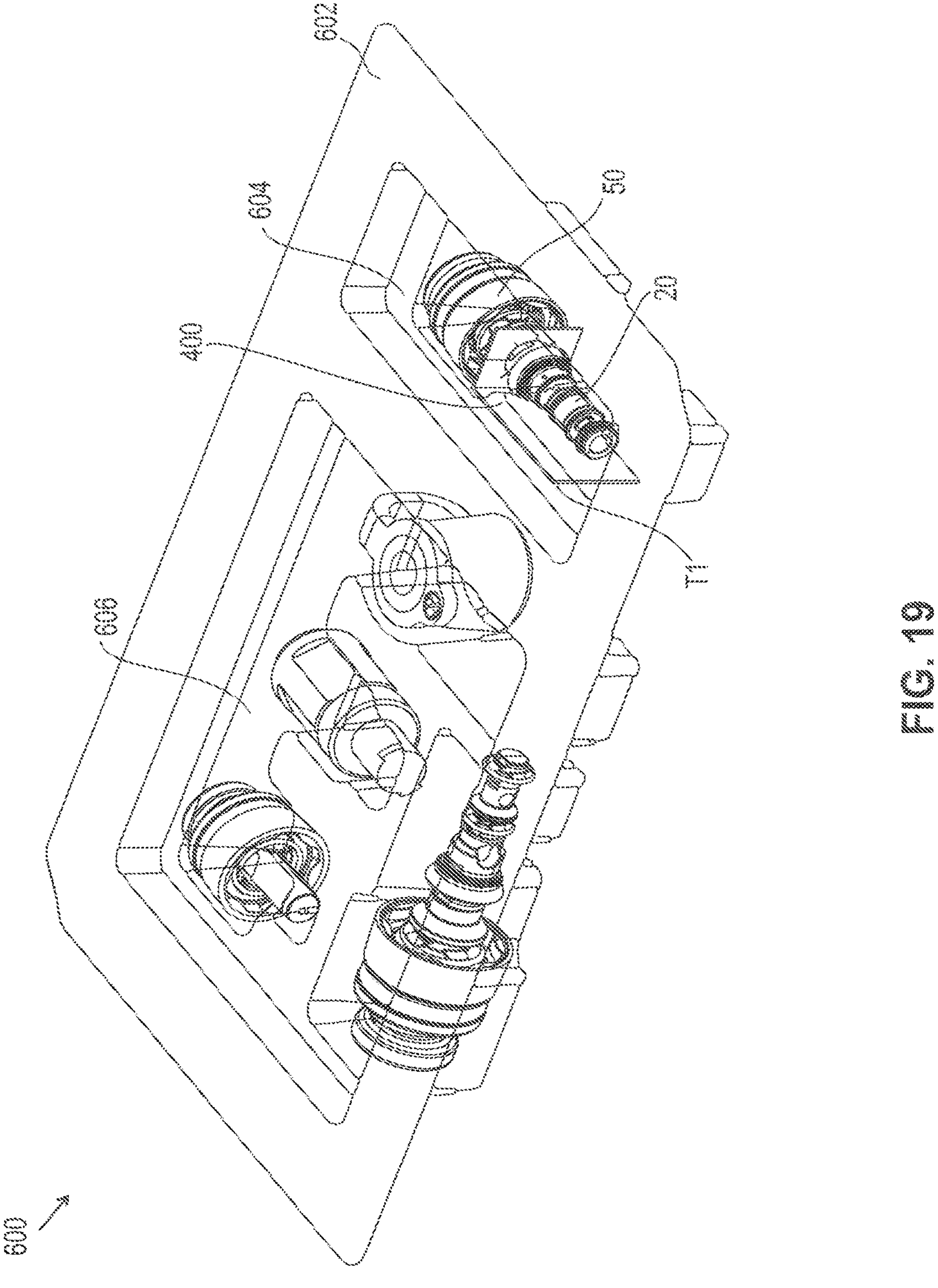
FIG. 19 illustrates a perspective view of the tag for an endoscope valve of FIG. 18 folded into an L-shaped configuration about a cleaning adapter that is disposed in a kit for an endoscope procedure.

Referring to FIGS. 18-19, a tag 400 is provided that is configured to receive a region of an endoscope valve, such as, for example, cleaning adapter 20, as described above. The tag acts as a physical barrier to prevent use of the cleaning adapter until the tag is torn off. In this way, the user has to take an additional step of removing the tag from the cleaning adapter as opposed to other valves in the kit that do not have any safety tag around them. Therefore, the tag prevents a user from incorrectly using the cleaning adapter instead of an air/water valve during an endoscope procedure.

The tag comprises a planar surface 402. The planar surface has a certain thickness T1, as shown in FIG. 19. In some embodiments, thickness T1 is from about 0.01 to about 0.5 inches. In some embodiments, thickness T1 is from about 0.01, 0.02, 0.03, 0.04, 0.05, 0.06, 0.07, 0.08, 0.09, 0.1, 0.2, 0.3, 0.4 to about 0.5 inches.

The planar surface includes a first edge 404, a second edge 406 opposing the first edge, a third edge 408 and a fourth edge 410 opposing the third edge, as shown in FIG. 18. The third edge is disposed on a proximal end 412 of the planar surface and the fourth edge is disposed on a distal end 414 of the planar surface.

The planar surface has a length L4 and a width W3. In some embodiments, L4 is from about 1 to about 3 inches. In some embodiments, length L4 is from about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 to about 3 inches. In some embodiments, width W3 is from about 0.3 to about 1 inch. In some embodiments, width W3 is from about 0.3, 0.4, 0.5, 0.6, 0.7, 0.8, 0.9 to about 1 inch.

The planar surface includes an opening 416 configured to receive a region of the cleaning adapter. For example, a region of the cleaning adapter, such as between one or more gaskets 48 such as the umbrella gasket disposed distal to the first through hole 28, and boot 50 can be received by the opening, as shown in FIG. 19. In some embodiments, the opening has a diameter D4 that is equal to or greater than a diameter of the region of the endoscope valve that is received by the opening. In some embodiments, diameter D4 is from about 0.2 to about 0.6 inches. In some embodiments, diameter D4 is from about 0.2, 0.3, 0.4, 0.5 to about 0.6 inches. In some embodiments, the opening is circular. In some embodiments, the opening can be oval or square.

A perforation 418 is disposed adjacent to and contacting the opening and is configured to engage the region of the cleaning adapter received by the opening. The perforation is configured to be torn when a user desires to remove the cleaning adapter from the tag. In some embodiments, the perforation imparts flexibility to the tag. The perforation includes a first end 420 and a second end 422. The first end extends to the third edge of the planar surface and the second end contacts the opening. In some embodiments, the perforation has a length L5. In some embodiments, length L5 is from about 4 millimeters (mm) to about 10 mm. In some embodiments, length L5 is from about 4, 5, 6, 7, 8, 9 to about 10 mm.

The planar surface includes a fold line 424. The fold line is disposed adjacent to the opening and extends perpendicular to an edge of the planar surface, such as, for example, the first edge and the second edge, as shown in FIG. 18. The fold line is configured to impart flexibility to the tag and in some embodiments, the tag can be formed into an L-shaped configuration by bending the fold line, as shown in FIG. 19. In some embodiments, the perforation is disposed perpendicular to the fold line.

In some embodiments, the fold line has a length L6. In some embodiments, length L6 is from about 0.3 to about 1 inch. In some embodiments, length L6 is from about 0.3, 0.4, 0.5, 0.6, 0.7, 0.8, 0.9 to about 1 inch. In some embodiments, the fold line length L6 can be the same size as the planar surface width W3.

In some embodiments, the planar surface comprises a plurality of slits 426 that are disposed in a circumferential array about the opening of the planar surface. The plurality of slits are configured to facilitate easy insertion of the region of the cleaning adapter that is received by the opening. In some embodiments, the plurality of slits contact the opening. The plurality of slits can include 2, 3, 4, 5, 6, 7, 8, 9 or 10 slits having the same or different length L7. In some embodiments, length L7 can be from about 1 mm to about 4 mm. In some embodiments, length L7 can be from about 1, 2, 3 or 4 mm. It is to be understood that the opening, the perforation, and the plurality of slits are disposed between the first edge and the second edge of the planar surface, and that the fold line extends from the first edge to the second edge.

In some embodiments, the distal end of the planar surface includes indicia 428 comprising text and/or a symbol that visually signals a warning to a user. In some embodiments, the indicia can be various fonts, sizes, colors and can be raised or flush with the planar surface. In some embodiments, the indicia can be printed in red, black, orange, yellow, blue, green, purple, brown, white and/or pink ink.

In some embodiments, the tag can be a certain color. In some embodiments, the color of the tag can include, but is not limited to red, black, orange, yellow, blue, green, purple, brown, white and/or pink.

In some embodiments, the tag can be made from a thick material to prevent the cleaning adapter from fully seating in a port of an endoscope if the tag is not removed before use. In some embodiments, the tag can be made from a material that does not create debris, particulate or tear during assembly, such as, for example, polyethylene. In some embodiments, the tag is made from a material that does not hinder the effectiveness of an ETO sterilization process and does not degrade/warp during sterilization, transport or storage (e.g., for up to a three-year shelf life). In some embodiments, the tag can be made from one or more materials including, but not limited to polypropylene, cardboard, construction paper, kraft paper, bond paper, gloss coated paper, card stock paper, chipboard, plastic, rubber, metal or a combination thereof. In some embodiments, the material that the tag is made from can be made waterproof. In some embodiments, one or more layers of plastic, rubber and/or wax can be added to the tag to waterproof the tag.

Figure 20:
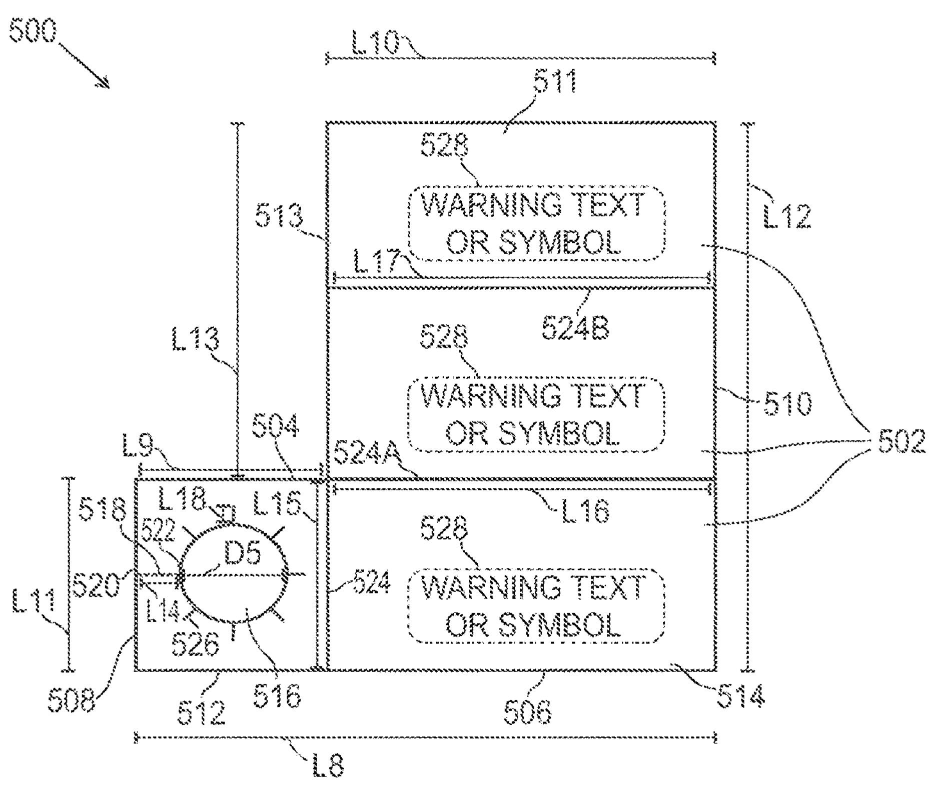
FIG. 20 illustrates a front view of an embodiment of a tag for an endoscope valve.
Figure 21:
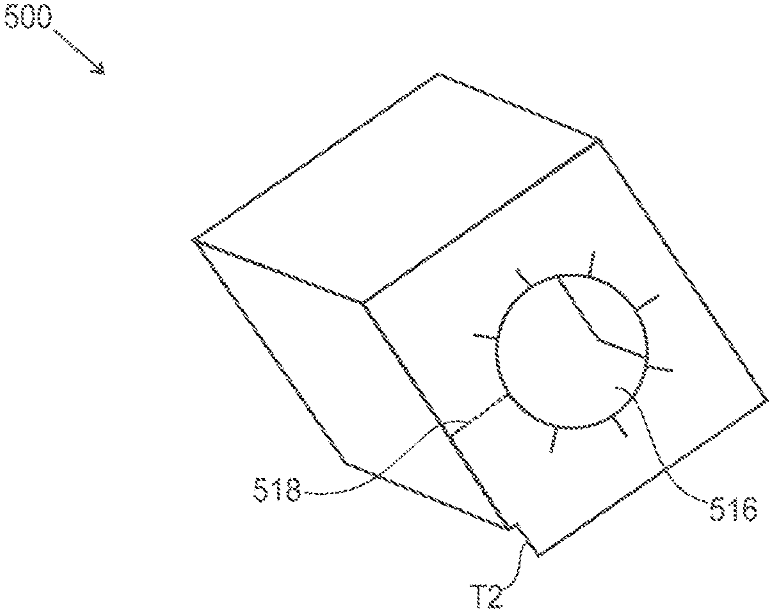
FIG. 21 illustrates a perspective view of the tag for an endoscope valve of FIG. 20 folded into a shaped configuration.
Figure 22:
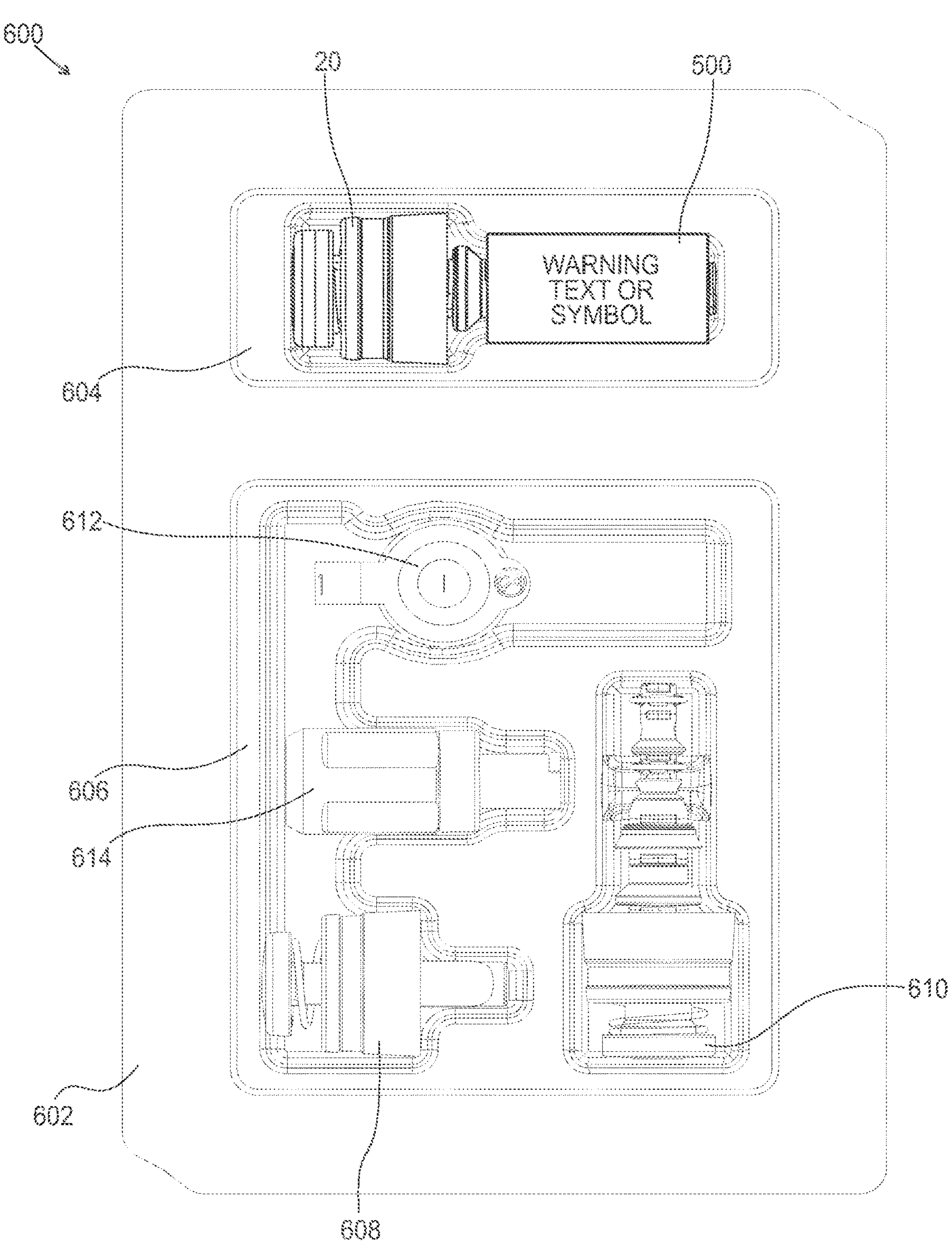
FIG. 22 illustrates a top view of the tag for an endoscope valve of FIG. 20 folded into a shaped configuration about a cleaning adapter that is disposed in a kit for an endoscope procedure.

Referring to FIGS. 20-22, a tag 500, similar to tag 400 is provided that is configured to receive a region of an endoscope valve, such as, for example, cleaning adapter 20, as described above. The tag comprises a planar surface 502. The planar surface has a certain thickness T2, as shown in FIG. 21. In some embodiments, thickness T2 is from about 0.01 to about 0.5 inches. In some embodiments, thickness T2 is from about 0.01, 0.02, 0.03, 0.04, 0.05, 0.06, 0.07, 0.08, 0.09, 0.1, 0.2, 0.3, 0.4 to about 0.5 inches.

The planar surface includes a first edge 504, a second edge 506 opposing the first edge, a third edge 508, a fourth edge 510 opposing the third edge, a fifth edge 511 opposing the second edge, and a sixth edge 513 opposing the fourth edge and adjacent to the first edge, as shown in FIG. 20. The third edge is disposed on a proximal end 512 of the planar surface and the fourth edge is disposed on a distal end 514 of the planar surface.

In some embodiments, the planar surface has a length L8 at the second edge. In some embodiments, L8 is from about 1 to about 3 inches. In some embodiments, length L8 is from about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 to about 3 inches. In some embodiments, the planar surface has a length L9 at the first edge. In some embodiments, length L9 is from about 0.3 to about 1 inch. In some embodiments, length L9 is from about 0.3, 0.4, 0.5, 0.6, 0.7, 0.8, 0.9 to about 1 inch. In some embodiments, L8 is greater in length than L9. In some embodiments, the planar surface has a length L10 at the fifth edge. In some embodiments, L10 is from about 0.6 to about 2 inches. In some embodiments, length L10 is from about 0.6, 0.7, 0.8, 0.9, 1, 1.1, 1.2, 1.3, 1.4, 1.5, 1.6, 1.7, 1.8, 1.9 to about 2 inches. In some embodiments, length L8 is greater than length L10 and length L9 is less than length L10.

In some embodiments, the planar surface has a length L11 at the third edge. In some embodiments, length L11 is from about 0.3 to about 1 inch. In some embodiments, length L11 is from about 0.3, 0.4, 0.5, 0.6, 0.7, 0.8, 0.9 to about 1 inch. In some embodiments, the planar surface has a length L12 at the fourth edge. In some embodiments, length L12 is from about 0.9 to about 3 inches. In some embodiments, length L12 is from about 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 to about 3 inches. In some embodiments, length L11 is less than length L12. In some embodiments, the planar surface has a length L13 at the sixth edge. In some embodiments, L13 is from about 0.6 to about 2 inches. In some embodiments, length L13 is from about 0.6, 0.7, 0.8, 0.9, 1, 1.1, 1.2, 1.3, 1.4, 1.5, 1.6, 1.7, 1.8, 1.9 to about 2 inches. In some embodiments, length L12 is greater than length L13 and length L11 is less than length L13.

The planar surface includes an opening 516 configured to receive a region of the cleaning adapter. For example, a region of the cleaning adapter, such as between one or more gaskets 48 such as the umbrella gasket disposed distal to the first through hole 28, and boot 50 can be received by the opening, as shown in FIG. 22. In some embodiments, the opening has a diameter D5 that is equal to or greater than a diameter of the region of the endoscope valve that is received by the opening. In some embodiments, diameter D5 is from about 0.2 to about 0.6 inches. In some embodiments, diameter D5 is from about 0.2, 0.3, 0.4, 0.5 to about 0.6 inches. In some embodiments, the opening is circular. In some embodiments, the opening can be oval or square.

A perforation 518 is disposed adjacent to and contacting the opening and is configured to engage the region of the cleaning adapter received by the opening. The perforation is configured to be torn when a user desires to remove the cleaning adapter from the tag. In some embodiments, the perforation imparts flexibility to the tag. The perforation includes a first end 520 and a second end 522. The first end extends to the third edge of the planar surface and the second end contacts the opening. In some embodiments, the perforation has a length L14. In some embodiments, length L14 is from about 4 millimeters to about 10 mm. In some embodiments, length L14 is from about 4, 5, 6, 7, 8, 9 to about 10 mm.

The planar surface includes a first fold line 524. The first fold line is disposed adjacent to the opening and extends perpendicular to an edge of the planar surface, such as, for example, the first edge and the second edge, as shown in FIG. 20. In some embodiments, the perforation is disposed perpendicular to the first fold line.

The planar surface includes a second fold line 524A that contacts the first fold line. In some embodiments, a third fold line 524B is provided. The third fold line extends parallel to the second fold line and allows the tag to be folded into a shaped configuration, as shown in FIGS. 21 and 22. In some embodiments, the fold lines are configured to impart flexibility to the tag, thereby allowing the tag to bend at the fold line to configure the shape. In some embodiments, the tag is configured to be folded and unfolded, and in the folded configuration, the tag partially encloses the endoscope valve.

In some embodiments, the first fold line has a length L15. In some embodiments, length L15 is from about 0.3 to about 1 inch. In some embodiments, length L15 is from about 0.3, 0.4, 0.5, 0.6, 0.7, 0.8, 0.9 to about 1 inch. In some embodiments, the first fold line length L15 can be the same size as the planar surface length L11.

In some embodiments, the second fold line has a length L16 and the third fold line has a length L17. In some embodiments, lengths L16, L17 are from about 0.6 to about 2 inches. In some embodiments, length L16, L17 are from about 0.6, 0.7, 0.8, 0.9, 1, 1.1, 1.2, 1.3, 1.4, 1.5, 1.6, 1.7, 1.8, 1.9 to about 2 inches. In some embodiments, lengths L16, L17 can be the same size as the planar surface length L10 and lengths L16, L17 are greater than length L15.

In some embodiments, the planar surface comprises a plurality of slits 526 that are disposed in a circumferential array about the opening of the planar surface. The plurality of slits are configured to facilitate easy insertion of the region of the cleaning adapter that is received by the opening. In some embodiments, the plurality of slits contact the opening. The plurality of slits can include 2, 3, 4, 5, 6, 7, 8, 9 or 10 slits having the same or different length L18.

In some embodiments, length L18 can be from about 1 mm to about 4 mm. In some embodiments, length L18 can be from about 1, 2, 3 or 4 mm. It is to be understood that the opening, the perforation, the plurality of slits are disposed between the first edge and the second edge of the planar surface, and that the first fold line extends from the first edge to the second edge.

In some embodiments, the distal end of the planar surface includes indicia 528 comprising text and/or a symbol that visually signals a warning to a user. In some embodiments, the indicia can be configured in the same manner as indicia 428, as described above with regard to tab 400.

Figure 23:
FIG. 23 illustrates a front view of an embodiment of a tag for an endoscope valve.
Figure 23:
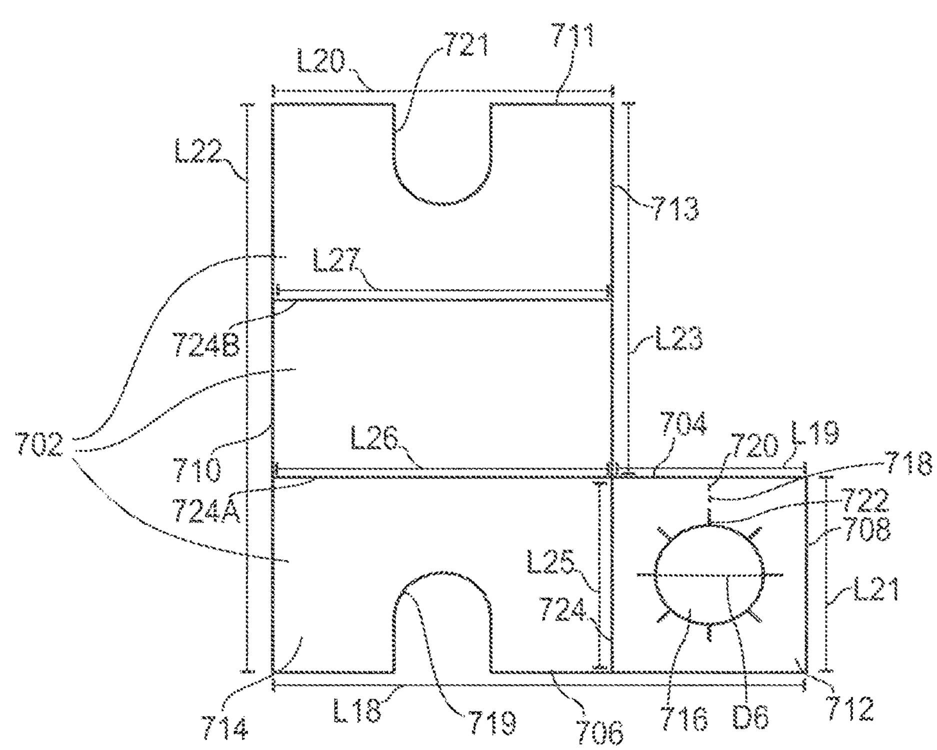
Figure 24:
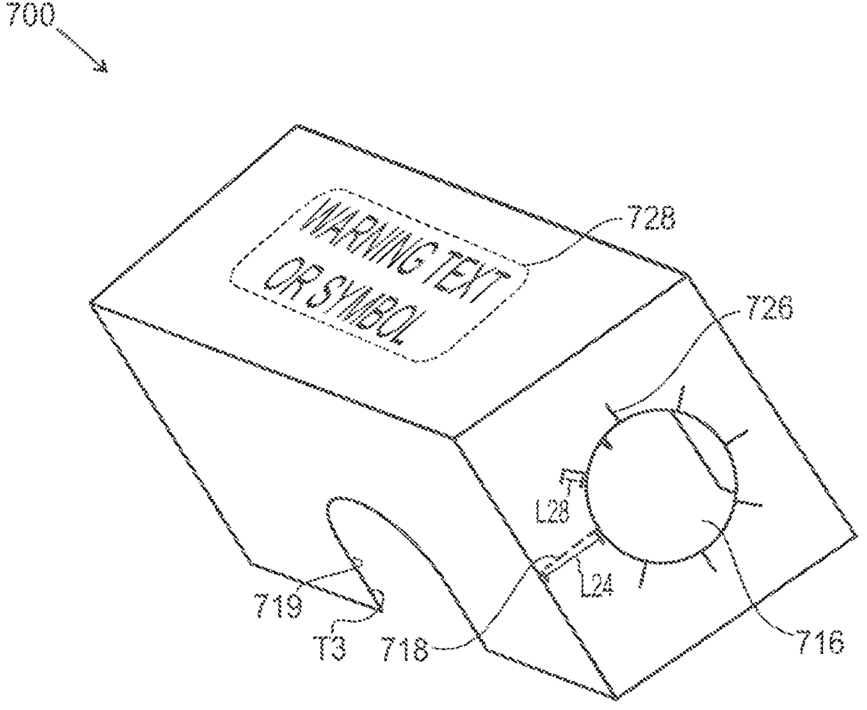
FIG. 24 illustrates a perspective view of the tag for an endoscope valve of FIG. 23 folded into a shaped configuration.
Figure 25:
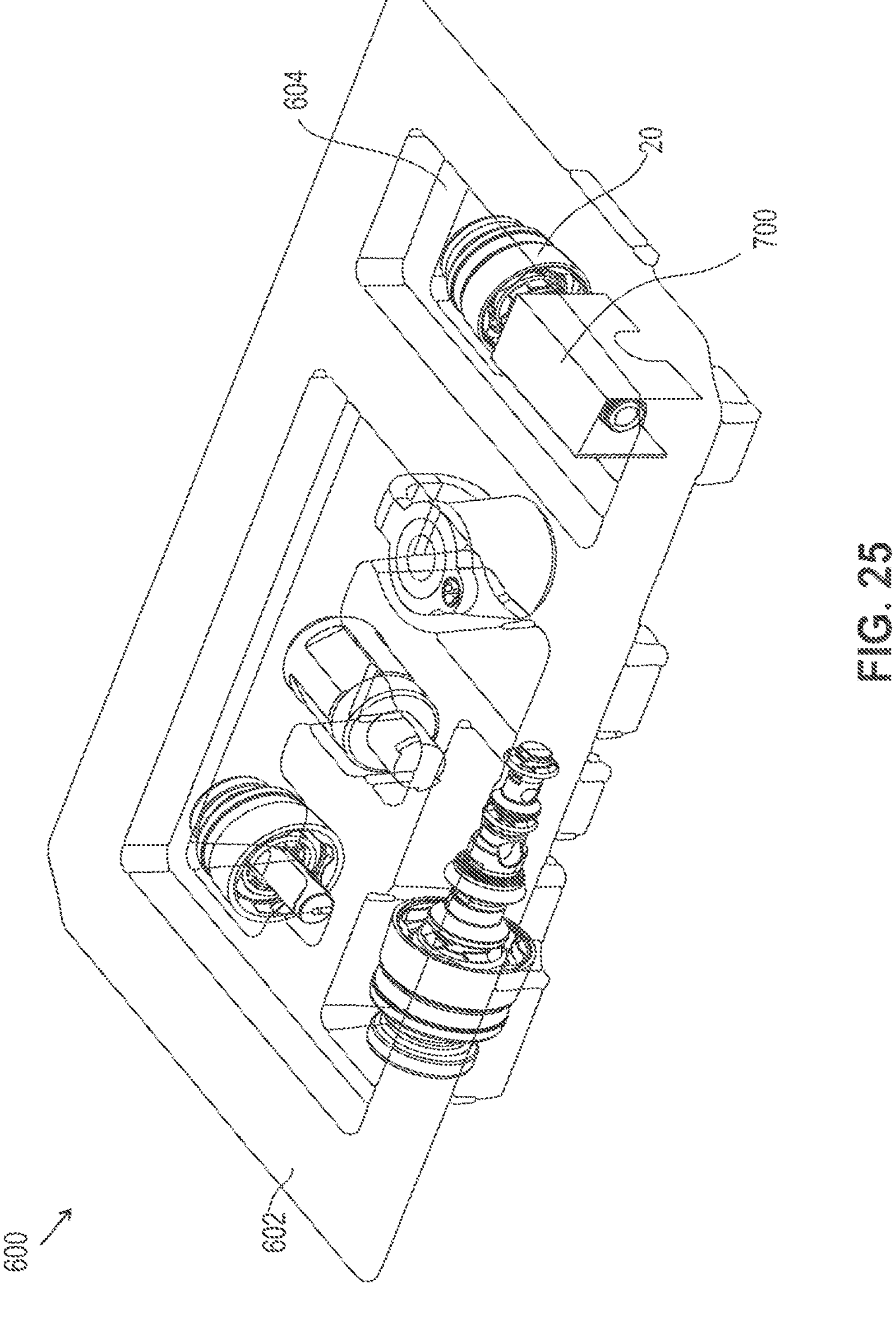
FIG. 25 illustrates a perspective view of the tag for an endoscope valve of FIG. 23 folded into a shaped configuration about a cleaning adapter that is disposed in a kit for an endoscope procedure.

Referring to FIGS. 23-25, a tag 700, similar to tag 500 is provided that is configured to receive a region of an endoscope valve, such as, for example, cleaning adapter 20, as described above. The tag comprises a planar surface 702. The planar surface has a certain thickness T3, as shown in FIG. 24. In some embodiments, thickness T3 is from about 0.01 to about 0.5 inches. In some embodiments, thickness T3 is from about 0.01, 0.02, 0.03, 0.04, 0.05, 0.06, 0.07, 0.08, 0.09, 0.1, 0.2, 0.3, 0.4 to about 0.5 inches.

The planar surface includes a first edge 704, a second edge 706 opposing the first edge, a third edge 708, a fourth edge 710 opposing the third edge, a fifth edge 711 opposing the second edge, and a sixth edge 713 opposing the fourth edge and adjacent to the first edge, as shown in FIG. 23. The third edge is disposed on a proximal end 712 of the planar surface and the fourth edge is disposed on a distal end 714 of the planar surface.

In some embodiments, the planar surface has a length L18 at the second edge. In some embodiments, L18 is from about 1 to about 3 inches. In some embodiments, length L18 is from about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 to about 3 inches. In some embodiments, the planar surface has a length L19 at the first edge. In some embodiments, length L19 is from about 0.3 to about 1 inch. In some embodiments, length L19 is from about 0.3, 0.4, 0.5, 0.6, 0.7, 0.8, 0.9 to about 1 inch. In some embodiments, L18 is greater in length than L19. In some embodiments, the planar surface has a length L20 at the fifth edge. In some embodiments, L20 is from about 0.6 to about 2 inches. In some embodiments, length L20 is from about 0.6, 0.7, 0.8, 0.9, 1, 1.1, 1.2, 1.3, 1.4, 1.5, 1.6, 1.7, 1.8, 1.9 to about 2 inches. In some embodiments, length L18 is greater than length L20 and length L19 is less than length L20.

In some embodiments, the planar surface has a length L21 at the third edge. In some embodiments, length L21 is from about 0.3 to about 1 inch. In some embodiments, length L21 is from about 0.3, 0.4, 0.5, 0.6, 0.7, 0.8, 0.9 to about 1 inch. In some embodiments, the planar surface has a length L22 at the fourth edge. In some embodiments, length L22 is from about 0.9 to about 3 inches. In some embodiments, length L22 is from about 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 to about 3 inches. In some embodiments, length L21 is less than length L22. In some embodiments, the planar surface has a length L23 at the sixth edge. In some embodiments, L23 is from about 0.6 to about 2 inches. In some embodiments, length L23 is from about 0.6, 0.7, 0.8, 0.9, 1, 1.1, 1.2, 1.3, 1.4, 1.5, 1.6, 1.7, 1.8, 1.9 to about 2 inches. In some embodiments, length L22 is greater than length L23 and length L21 is less than length L23.

The planar surface includes an opening 716 configured to receive a region of the cleaning adapter. For example, a region of the cleaning adapter, such as between one or more gaskets 48 such as the umbrella gasket disposed distal to the first through hole 28, and boot 50 can be received by the opening, as shown in FIG. 25. In some embodiments, the opening has a diameter D6 that is equal to or greater than a diameter of the region of the endoscope valve that is received by the opening. In some embodiments, diameter D6 is from about 0.2 to about 0.6 inches. In some embodiments, diameter D6 is from about 0.2, 0.3, 0.4, 0.5 to about 0.6 inches. In some embodiments, the opening is circular. In some embodiments, the opening can be oval or square.

A perforation 718 is disposed adjacent to and contacting the opening and is configured to engage the region of the cleaning adapter received by the opening. The perforation is configured to be torn when a user desires to remove the cleaning adapter from the tag. In some embodiments, the perforation is disposed parallel to a first fold line, as described herein. In some embodiments, the perforation imparts flexibility to the tag. The perforation includes a first end 720 and a second end 722. The first end extends to the first edge of the planar surface and the second end contacts the opening. In some embodiments, the perforation has a length L24, as shown in FIG. 24. In some embodiments, length L24 is from about 4 millimeters to about 10 mm. In some embodiments, length L24 is from about 4, 5, 6, 7, 8, 9 to about 10 mm.

The planar surface includes a first recess 719 and a second recess 721, as shown in FIG. 23. The first recess and/or the second recess are disposed adjacent to the opening and are configured to facilitate an optimal fit in a compartment 604 of a tray 602, shown in FIG. 25, described below. In some embodiments, the first recess is parallel to the second recess and each recess can be arch shaped. In some embodiments, a portion of the second edge includes the first recess and a portion of the fifth edge includes the second recess. In some embodiments, the planar surface can include 1 to about 6 recesses. In some embodiments, the planar surface can include 1, 2, 3, 4, 5 to about 6 recesses.

The planar surface includes a first fold line 724. The first fold line is disposed adjacent to the opening and extends perpendicular to an edge of the planar surface, such as, for example, the first edge and the second edge, as shown in FIG. 23. In some embodiments, the perforation is disposed perpendicular to the first fold line.

The planar surface includes a second fold line 724A that contacts the first fold line. In some embodiments, a third fold line 724B is provided. The third fold line extends parallel to the second fold line and allows the tag to be folded into a shaped configuration, as shown in FIGS. 24 and 25. In some embodiments, the fold lines are configured to impart flexibility to the tag, thereby allowing the tag to bend at the fold line to configure the shape. In some embodiments, the tag is configured to be folded and unfolded, and in the folded configuration, the tag partially encloses the endoscope valve.

In some embodiments, the first fold line has a length L25. In some embodiments, length L25 is from about 0.3 to about 1 inch. In some embodiments, length L25 is from about 0.3, 0.4, 0.5, 0.6, 0.7, 0.8, 0.9 to about 1 inch. In some embodiments, the first fold line length L25 can be the same size as length L21.

In some embodiments, the second fold line has a length L26 and the third fold line has a length L27. In some embodiments, lengths L26, L27 are from about 0.6 to about 2 inches. In some embodiments, length L26, L27 are from about 0.6, 0.7, 0.8, 0.9, 1, 1.1, 1.2, 1.3, 1.4, 1.5, 1.6, 1.7, 1.8, 1.9 to about 2 inches. In some embodiments, lengths L26, L27 can be the same size as length L20 and lengths L26, L26 are greater than length L25.

In some embodiments, the planar surface comprises a plurality of slits 726 that are disposed in a circumferential array about the opening of the planar surface. The plurality of slits are configured to facilitate easy insertion of the region of the cleaning adapter that is received by the opening. In some embodiments, the plurality of slits contact the opening. The plurality of slits can include 2, 3, 4, 5, 6, 7, 8, 9 or 10 slits having the same or different length L28. In some embodiments, length L28 can be from about 1 mm to about 4 mm. In some embodiments, length L28 can be from about 1, 2, 3 or 4 mm. It is to be understood that the opening, the perforation, the first fold line, and the plurality of slits are disposed between the first edge and the second edge of the planar surface, and that the first fold line extends from the first edge to the second edge.

In some embodiments, the distal end of the planar surface includes indicia 728 comprising text and/or a symbol that visually signals a warning to a user, as shown in FIG. 24. In some embodiments, the indicia can be configured in the same manner as indicia 428, as described above with regard to tab 400.

Figure 26:
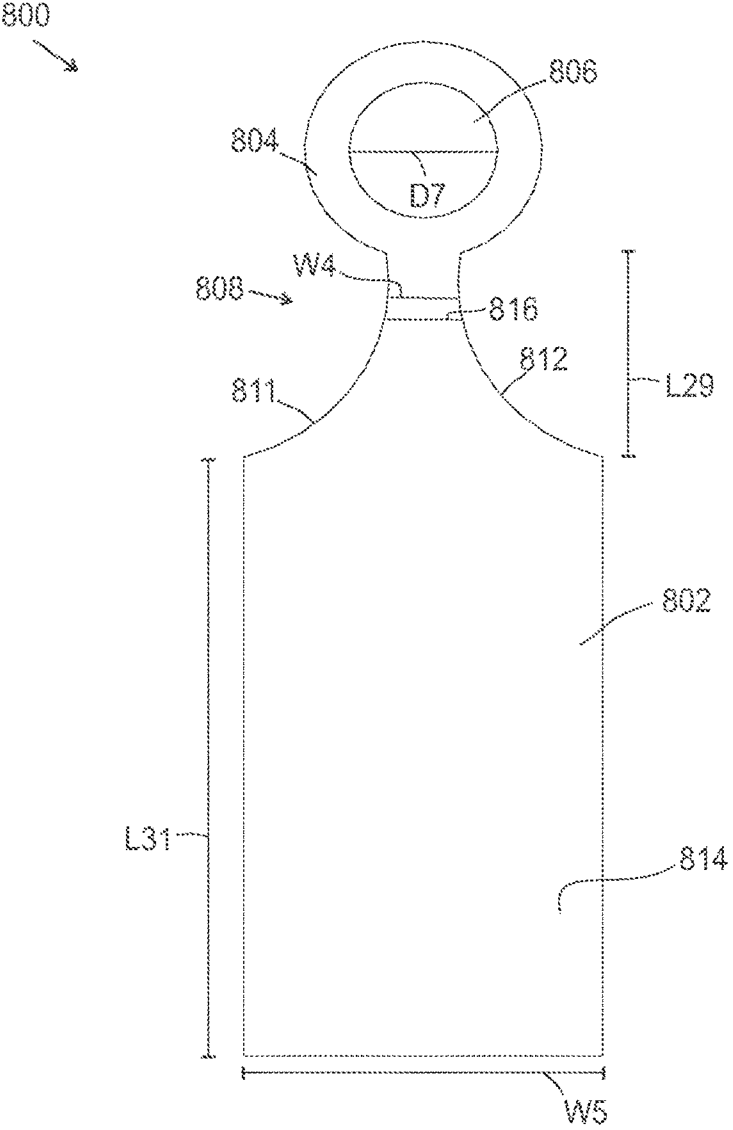
FIG. 26 illustrates a front view of an embodiment of a tag for an endoscope valve.
Figure 27:
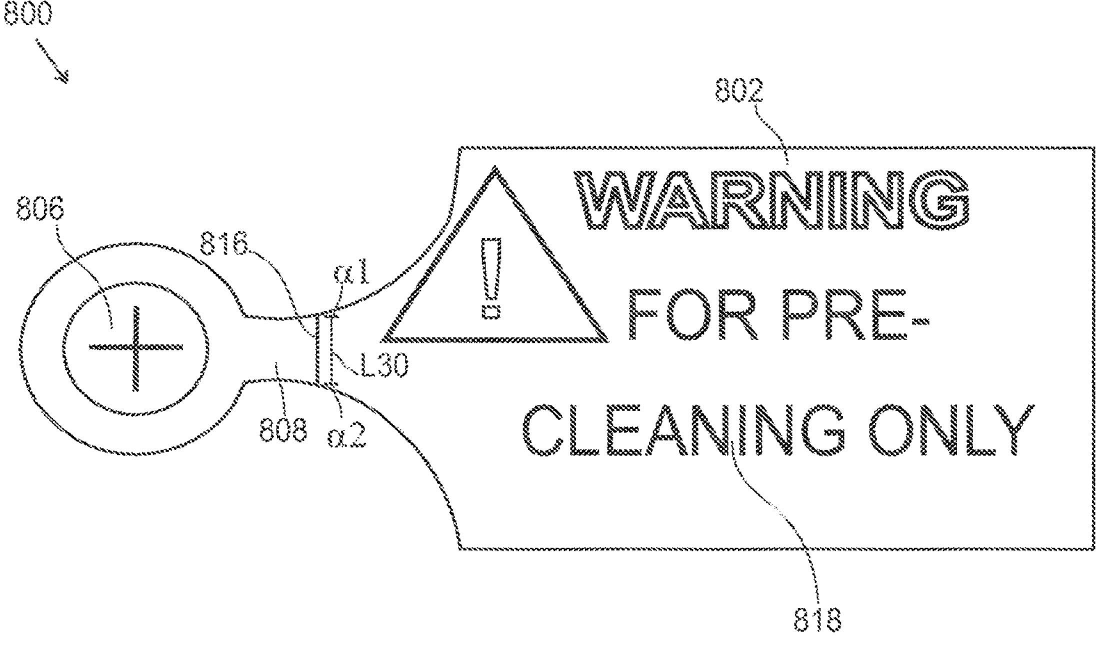
FIG. 27 illustrates a front view of the tag of FIG. 26 with indicia printed on the tag in the form of text and/or a symbol that visually signals a warning to a user.
Figure 28:
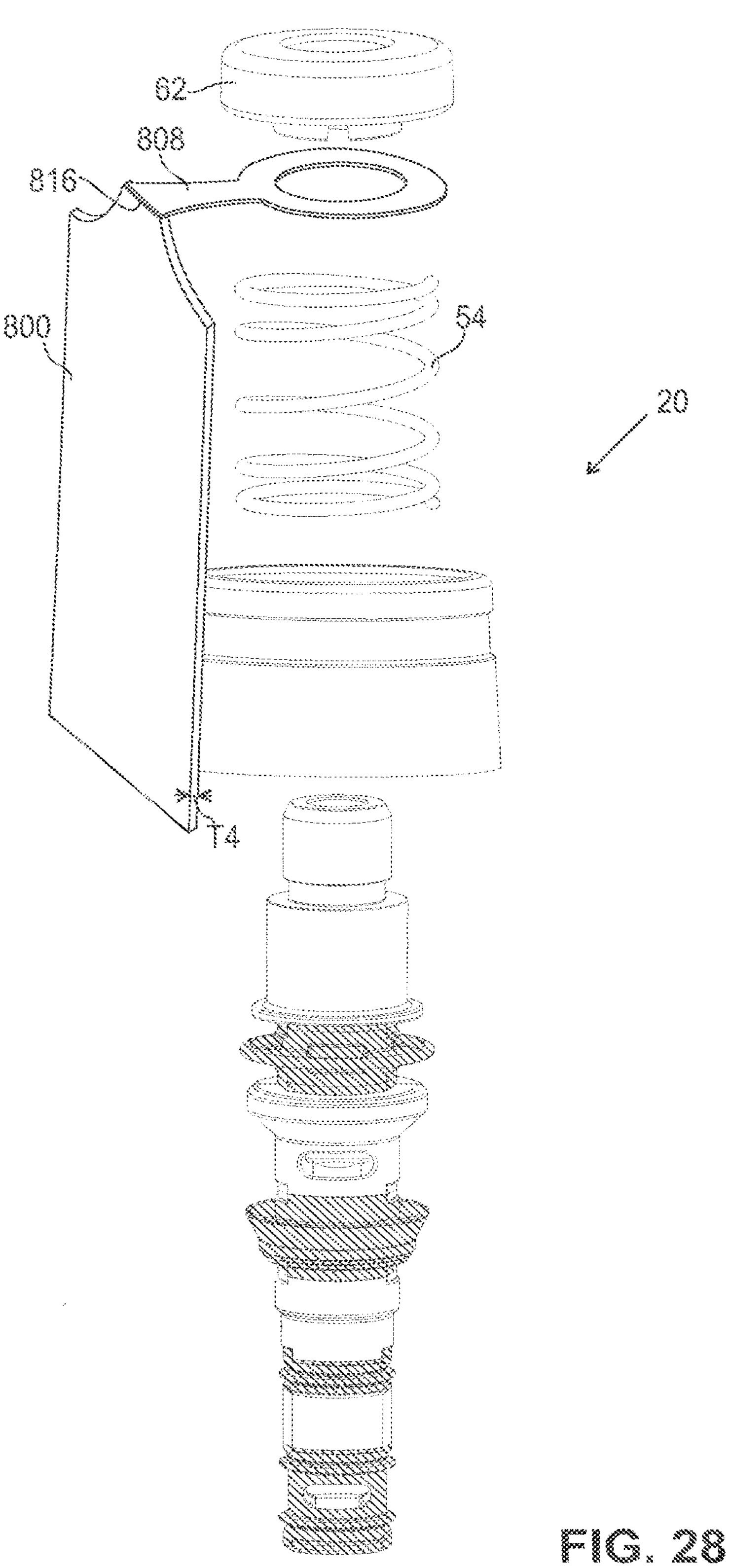
FIG. 28 illustrates an exploded perspective view of the tag of FIG. 26 disposed with a cleaning adapter.

Referring to FIGS. 26-33, a tag 800 is provided that is configured to receive a region of an endoscope valve, such as, for example, cleaning adapter 20, as described above. The tag comprises a planar surface 802. The planar surface has a certain thickness T4, as shown in FIG. 28. In some embodiments, thickness T4 is from about 0.01 to about 0.5 inches. In some embodiments, thickness T4 is from about 0.01, 0.02, 0.03, 0.04, 0.05, 0.06, 0.07, 0.08, 0.09, 0.1, 0.2, 0.3, 0.4 to about 0.5 inches.

Figure 29:
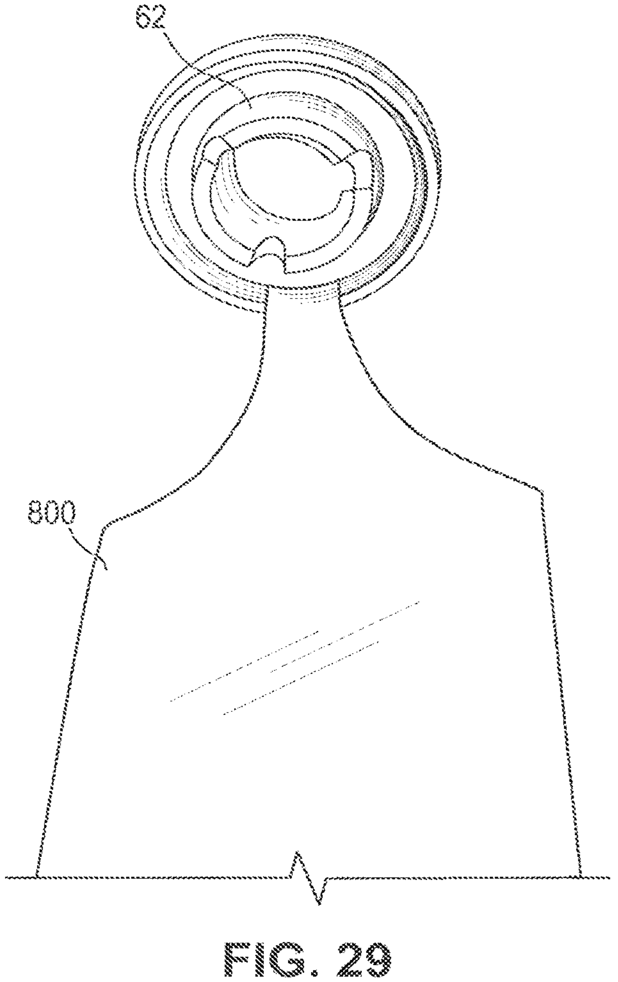
FIG. 29 illustrates a perspective view of a section of the tag of FIG. 26 disposed with a portion, such as a button cap of a cleaning adapter.

The planar surface comprises a proximal end 804 having an opening 806 configured to receive a region of the cleaning adapter. For example, the region of the cleaning adapter received by the opening can be a distal end of button cap 62 and a portion of resilient member 54, as shown in FIGS. 28 and 29. The button cap is removed from the cleaning adapter and the opening of the tag engages with the distal end of the button cap and a portion of the resilient member.

In some embodiments, the opening has a diameter D7 that is less than, equal to or greater than a diameter of the region of the endoscope valve that is received by the opening. In some embodiments, diameter D7 is from about 0.2 to about 0.6 inches. In some embodiments, diameter D7 is from about 0.2, 0.3, 0.4, 0.5 to about 0.6 inches.

In some embodiments, the proximal end and the opening are circular shaped, as shown in FIGS. 26-29. In the circular shaped configuration, diameter D7 of the opening is equal to or greater than a diameter of the region of the endoscope valve that is received by the opening and the engagement is snug.

Figure 31:
FIG. 31 illustrates a front view of an embodiment of a tag for an endoscope valve.
Figure 31:
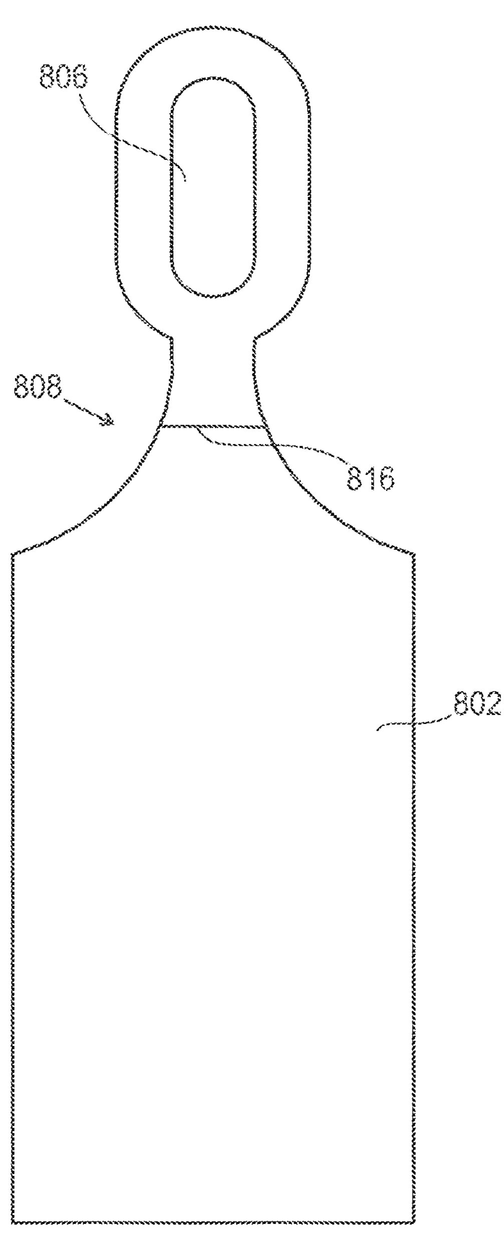

In some embodiments, the proximal end and the opening are slot shaped, as shown in FIG. 31. In the slot shaped configuration, diameter D7 of the opening is less than a diameter of the region of the endoscope valve that is received by the opening.

Figure 32:
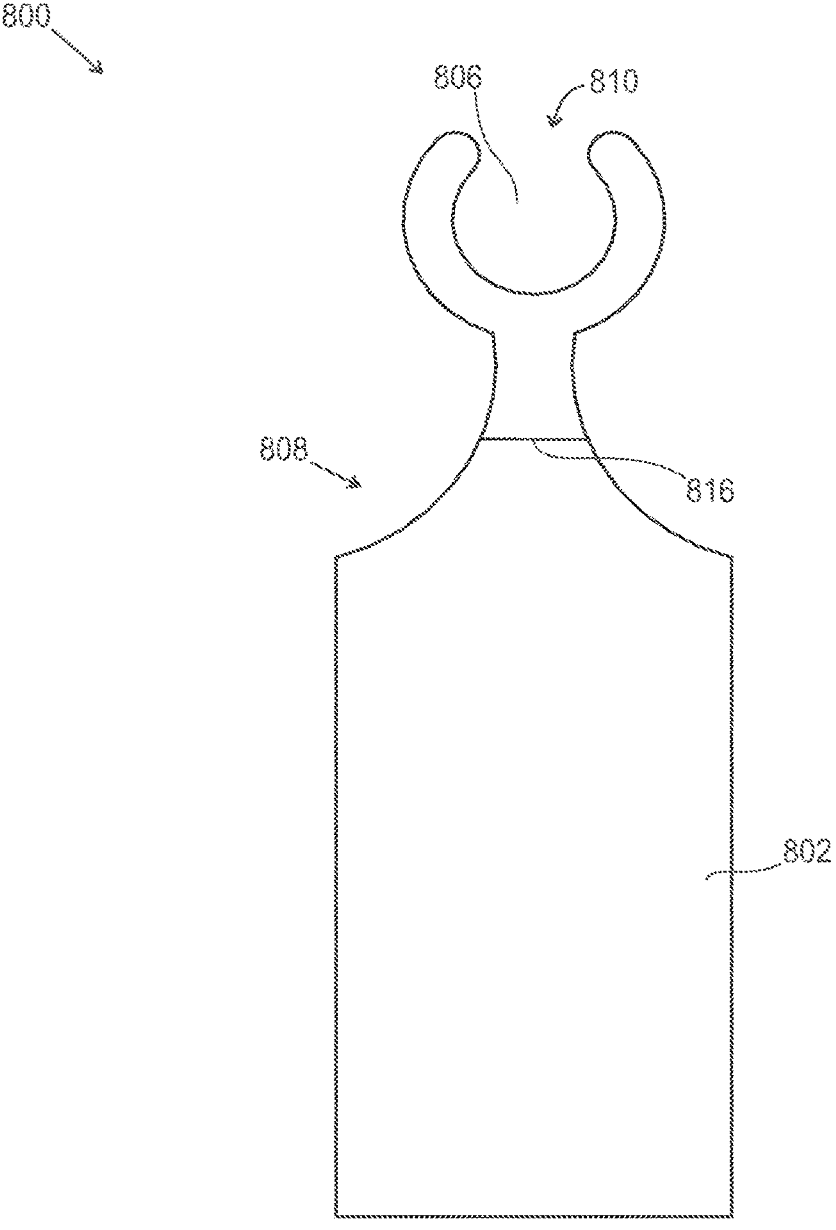
FIG. 32 illustrates a front view of an embodiment of a tag for an endoscope valve.

In some embodiments, the proximal end and the opening are semi-circular, forming a clip 810, as shown in FIG. 32. In the semi-circular or clip configuration, diameter D7 of the opening is equal to or greater than a diameter of the region of the endoscope valve that is received by the opening.

Figure 33:
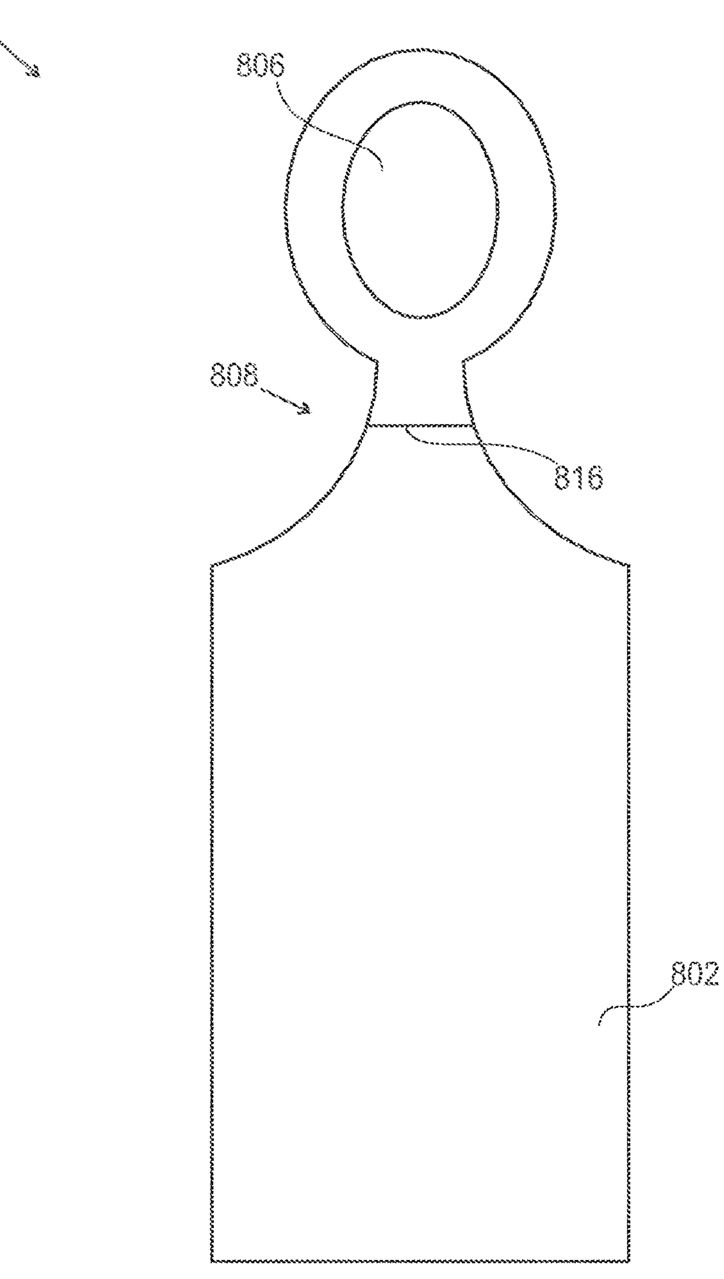
FIG. 33 illustrates a front view of an embodiment of a tag for an endoscope valve.

In some embodiments, the proximal end and the opening are oval shaped, as shown in FIG. 33. In the oval shaped configuration, diameter D7 of the opening is less than a diameter of the region of the endoscope valve that is received by the opening.

A tapered portion 808 is disposed adjacent to the opening. The tapered portion includes an edge, such as a first angled edge 811 and a second angled edge 812. The second angled edge is parallel to the first angled edge. In some embodiments, the first and second angled edges can have certain angles $\alpha$1 and $\alpha$2, as shown in FIG. 27. In some embodiments, angles $\alpha$1 and $\alpha$2 are the same and are from about 10 degrees to about 45 degrees. In some embodiments, angles $\alpha$1 and $\alpha$2 are from about 10, 12, 14, 16, 18, 20, 22, 24, 26, 28, 30, 32, 34, 36, 38, 40, 42, 44 to about 45 degrees.

The tapered portion can have a certain width W4 that can increase toward a distal end 814 of the planar surface, and a certain length L29. Width W4 can be from about 0.1 to about 0.6 inches. In some embodiments, width W4 can be from about 0.1, 0.2, 0.3, 0.4, 0.5 to about 0.6 inches. Length L29 can be from about 0.2 to about 1 inch. In some embodiments, length L29 can be from about 0.2, 0.3, 0.4, 0.5, 0.6, 0.7, 0.8, 0.9 to about 1 inch.

The tapered portion includes a fold line 816 disposed thereon, as shown in FIG. 28. The fold line extends perpendicular to the first angled edge and the second angled edge. In some embodiments, the planar surface is configured to bend at the fold line and the fold line imparts flexibility to the tag. The fold line can have a certain length L30, as shown in FIG. 27. In some embodiments, length L30 can be from about 0.1 to about 0.6 inches and is equal to the width W4 of the tapered portion. In some embodiments, length L30 can be from about 0.1, 0.2, 0.3, 0.4, 0.5 to about 0.6 inches. In some embodiments, the tapered portion does not include a fold line, as shown in FIG. 29.

The distal end of the planar surface can have a length L31 and a width W5, as shown in FIG. 26. Length L31 can be from about 1 to about 3 inches. In some embodiments, length L31 can be from about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 to about 3 inches. In some embodiments, width W5 can be from about 0.3 to about 1 inch. In some embodiments, width W5 is from about 0.3, 0.4, 0.5, 0.6, 0.7, 0.8, 0.9 to about 1 inch.

In some embodiments, the distal end includes indicia 818 comprising text and/or a symbol that visually signals a warning to a user, as shown in FIG. 27. In some embodiments, the indicia can be configured in the same manner as indicia 428, as described above with regard to tab 400.

Safety Tag Methods and Kits

A method of cleaning an endoscope is provided, the method comprising removing a tag from a cleaning adapter, the tag comprising a planar surface having an opening receiving a region of the cleaning adapter; a perforation disposed adjacent to and contacting the opening, the perforation engaging the region of the endoscope valve; and a fold line disposed adjacent to the opening and extending perpendicular to an edge of the planar surface.

In some embodiments, the method further comprises removing an air/water valve from an air/water cylinder of an endoscope. In some embodiments, the tag is removed from the cleaning adapter by applying a tearing force to the tag at the perforation. In some embodiments, the tag is removed from the cleaning adapter by applying a tearing force to the opening of the tag disposed at a proximal end. In some embodiments, a tearing force is applied to the proximal end and the proximal end is in a circular shape (FIGS. 26-29), a slot shape, (FIG. 31), a semi-circular shape, forming a clip (FIG. 32), or an oval shape (FIG. 33).

In some embodiments, after tearing, the method further comprises inserting a portion of a main stem of a cleaning adapter into the air/water cylinder of the endoscope; and directing air and/or water into a first through hole and out of a second through hole of the cleaning adapter and through the air/water cylinder of the endoscope to flush the endoscope.

In some embodiments, the perforation is disposed perpendicular to the fold line. In some embodiments, the planar surface comprises a plurality of slits disposed in a circumferential array about the opening of the planar surface, and the plurality of slits contacts the opening. In some embodiments, a distal end of the planar surface of the tag includes indicia comprising text and/or a symbol that visually signals a warning to a user. It is to be understood that the tag is tag 400 shown in FIG. 19. Alternatively, the tag can be tag 500 shown in FIG. 22, tag 700 shown in FIG. 25 or tag 800 shown in FIGS. 26-33.

A kit 600 for an endoscope is provided, as shown in FIGS. 17, 19, 22, 25 and 30. The kit comprises a tray 602 having a compartment 604. The compartment is configured for receiving cleaning adapter 20. The cleaning adapter engages a tag, the tag comprising a planar surface having an opening receiving a region of the cleaning adapter, a perforation disposed adjacent to and contacting the opening, the perforation engaging the region of the cleaning adapter, and a fold line disposed adjacent to the opening and extending perpendicular to an edge of the planar surface. In some embodiments, the compartment receives both the cleaning adapter and the tag. In some embodiments, the compartment partially encloses the cleaning adapter and the tag.

Figure 30:
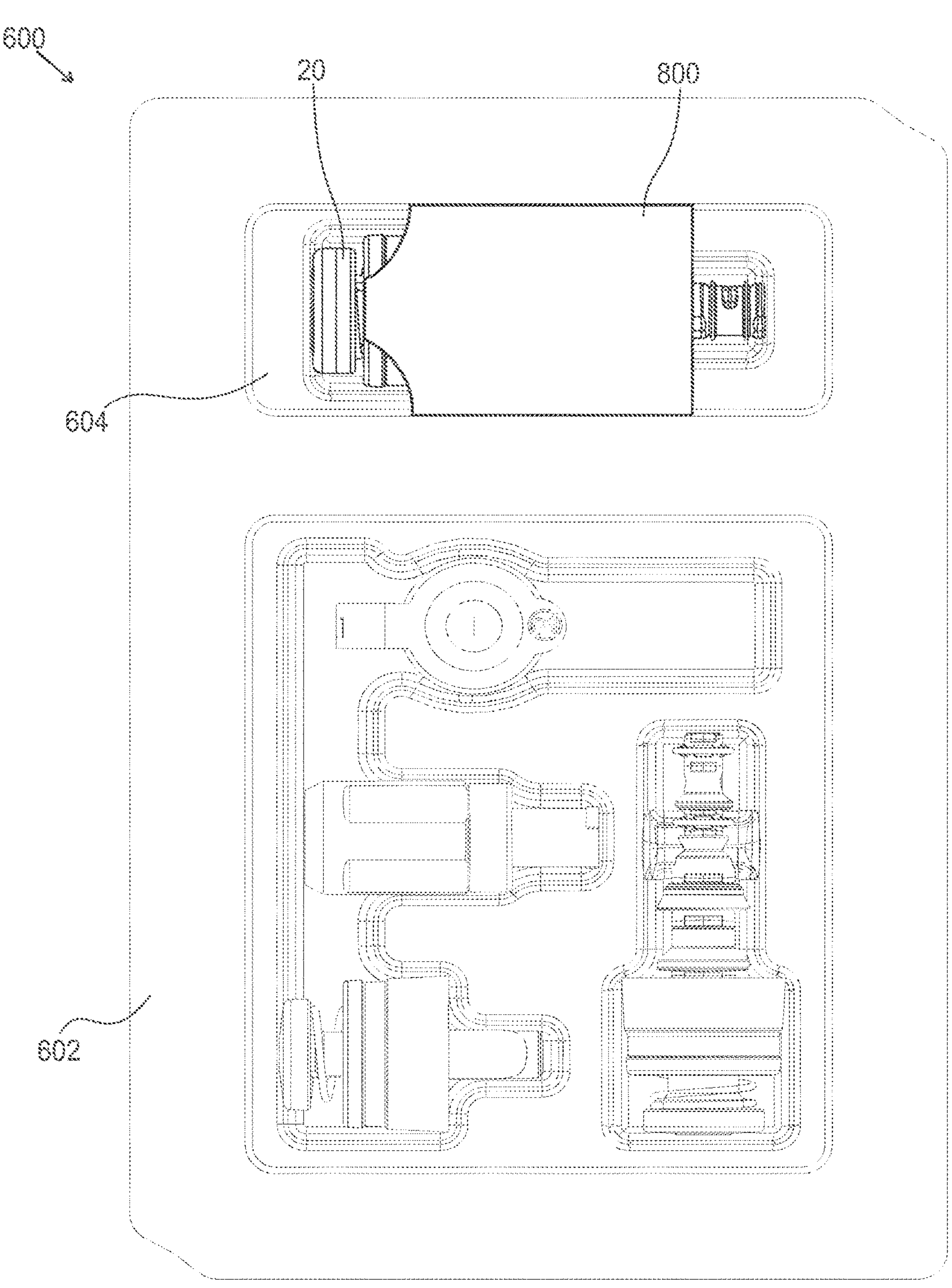
FIG. 30 illustrates a perspective view of the tag for an endoscope valve of FIG. 26 folded about a cleaning adapter that is disposed in a kit for an endoscope procedure.

In some embodiments, the perforation is disposed perpendicular to the fold line. In some embodiments, the planar surface comprises a plurality of slits disposed in a circumferential array about the opening of the planar surface, and the plurality of slits contacts the opening. In some embodiments, a distal end of the planar surface of the tag includes indicia comprising text and/or a symbol that visually signals a warning to a user. It is to be understood that the tag is tag 400, as shown in FIG. 19. In some embodiments, the tag can be tag 500, as shown in FIG. 22 or tag 700, as shown in FIG. 25. Alternatively, the tag is tag 800, as shown in FIG. 30.

In some embodiments, the kit further comprises a second compartment 606 for receiving a suction valve 608, an air/water valve 610, a biopsy valve 612 and/or an auxiliary connector 614, as shown in FIG. 22. In some embodiments, additional components can be added to the kit. Suitable disposable air/water valves and disposable suction valves and/or biopsy valves are available from Medivators Inc. located at 14605 28th Avenue North, Minneapolis, Minnesota 55447 and described in U.S. Pat. Nos. 9,585,545 and 9,408,523. These disclosures are herein incorporated by reference into the present disclosure.

In various embodiments, a kit is provided that may include additional parts along with the tag attached to the cleaning adapter combined together to be used with the cleaning adapter. The kit may include the cleaning adapter attached to the tag in a first compartment. A second compartment may include one or more containers holding a disinfectant and/or a detergent. A third compartment may include a disposable air/water valve. A fourth compartment may include a disposable suction valve and any other instruments needed for the procedure. A fifth compartment may include gloves, drapes, and other procedural supplies for endoscope procedures, as well as an instruction booklet or notification of a website where instructions for using the cleaning adapter can be located. A cover of the kit may include illustrations of the use of the cleaning adapter and a clear plastic cover may be placed over the compartments to maintain sterility.

Implementations described herein are included to demonstrate particular aspects of the present disclosure. It should be appreciated by those of skill in the art that the implementations described herein merely represent exemplary implementation of the disclosure. Those of ordinary skill in the art should, in light of the present disclosure, appreciate that many changes can be made in the specific implementations described and still obtain a like or similar result without departing from the spirit and scope of the present disclosure. From the foregoing description, one of ordinary skill in the art can easily ascertain the essential characteristics of this disclosure, and without departing from the spirit and scope thereof, can make various changes and modifications to adapt the disclosure to various usages and conditions. The implementations described hereinabove are meant to be illustrative only and should not be taken as limiting of the scope of the disclosure, which is defined in the following claims.

From the foregoing description, one of ordinary skill in the art can easily ascertain the essential characteristics of this disclosure, and without departing from the spirit and scope thereof, can make various changes and modifications to adapt the disclosure to various usages and conditions. The implementations described hereinabove are meant to be illustrative only and should not be taken as limiting of the scope of the disclosure, which is defined in the following claims.

What is claimed is:

1. A tag for an endoscope valve, the tag comprising a planar surface having an opening configured to receive a region of the endoscope valve; a perforation disposed adjacent to and contacting the opening, the perforation configured to engage the region of the endoscope valve; a first fold line disposed adjacent to the opening and extending perpendicular to an edge of the planar surface; a second fold line contacting the first fold line; and a first recess and a second recess, the first recess and/or the second recess disposed adjacent to the opening, wherein the tag is configured to be folded and unfolded, and in the folded configuration, the tag partially encloses the endoscope valve.

2. The tag of claim 1, wherein the first recess is parallel to the second recess.

3. The tag of claim 1, wherein the first recess and the second recess are arch shaped.

4. The tag of claim 1, wherein the edge is a first edge, and the planar surface comprises a second edge opposing the first edge, and the opening, the perforation, the first fold line, and a plurality of slits are disposed between the first edge and the second edge.

5. The tag of claim 4, wherein a portion of the second edge includes the first recess.

6. The tag of claim 4, wherein the planar surface comprises a third edge, a fourth edge, a fifth edge and a sixth edge, a portion of the fifth edge including the second recess.

7. The tag of claim 1, wherein the perforation is disposed parallel to the first fold line.

8. The tag of claim 1, wherein the planar surface comprises a plurality of slits disposed in a circumferential array about the opening of the planar surface.

9. The tag of claim 8, wherein the plurality of slits contacts the opening.

* * * * *